(12) United States Patent
Salituro et al.

(10) Patent No.: US 10,696,712 B2
(45) Date of Patent: Jun. 30, 2020

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Cambridge, MA (US); Gabriel Martinez Botella, Wayland, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/742,422

(22) PCT Filed: Jul. 6, 2016

(86) PCT No.: PCT/US2016/041160
§ 371 (c)(1),
(2) Date: Jan. 5, 2018

(87) PCT Pub. No.: WO2017/007832
PCT Pub. Date: Jan. 12, 2017

(65) Prior Publication Data
US 2018/0201643 A1    Jul. 19, 2018

Related U.S. Application Data

(60) Provisional application No. 62/189,065, filed on Jul. 6, 2015.

(51) Int. Cl.
| C07J 9/00 | (2006.01) |
| C07J 31/00 | (2006.01) |
| C07J 41/00 | (2006.01) |
| C07J 51/00 | (2006.01) |
| A61P 25/00 | (2006.01) |
| A61P 1/00 | (2006.01) |

(52) U.S. Cl.
CPC ............... *C07J 9/005* (2013.01); *A61P 1/00* (2018.01); *A61P 25/00* (2018.01); *C07J 9/00* (2013.01); *C07J 31/006* (2013.01); *C07J 41/0055* (2013.01); *C07J 51/00* (2013.01); *Y02P 20/582* (2015.11)

(58) Field of Classification Search
CPC ..... C07J 9/00; C07J 9/005; C07J 31/00; C07J 41/00; C07J 51/00; A61P 1/00; A61P 25/00; A61P 25/20
See application file for complete search history.

(56) References Cited

U.S. PATENT DOCUMENTS

| 2,594,323 A | 4/1952 | Levin et al. |
| 3,079,385 A | 2/1963 | Bertin et al. |
| 3,206,459 A | 9/1965 | Cross |
| 4,071,625 A | 1/1978 | Grunwell et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,227,375 B2 | 3/2019 | Martinez Botella et al. |
| 10,259,840 B2 | 4/2019 | Harrison et al. |
| 2004/0048838 A1 | 3/2004 | Gronvald et al. |

(Continued)

FOREIGN PATENT DOCUMENTS

| FR | 2850023 A1 | 7/2004 |
| JP | 8268917 A | 10/1996 |
| JP | 2005508368 A | 3/2005 |
| RU | 2194712 C2 | 12/2002 |
| WO | 9427608 A1 | 12/1994 |
| WO | 1995002409 A2 | 1/1995 |
| WO | 1995021617 A1 | 8/1995 |
| WO | 9612705 A1 | 5/1996 |
| WO | 9700884 A1 | 1/1997 |
| WO | 199905849 | 11/1999 |
| WO | 2000068246 A1 | 11/2000 |
| WO | 2001049703 A2 | 7/2001 |

(Continued)

OTHER PUBLICATIONS

Sepe et al., Total Synthesis and Pharmacological Characterization of Solomonsterol A, a Potent Marine Pregnane-X-Receptor Agonist Endowed with Anti-Inflammatory Activity. J. Med. Chem., vol. 54, pp. 4590-4599 (Year: 2011).*

(Continued)

*Primary Examiner* — Barbara P Badio
(74) *Attorney, Agent, or Firm* — Goodwin Procter LLP

(57) ABSTRACT

Compounds are provided according to Formula (I) and pharmaceutically acceptable salts thereof, and pharmaceutical compositions thereof; wherein $R^1$, $R^2$, $R^3$, $R^4$, $R^5$, and $R^8$ are as defined herein. Compounds of the present invention are contemplated useful for the prevention and treatment of a variety of conditions.

(I)

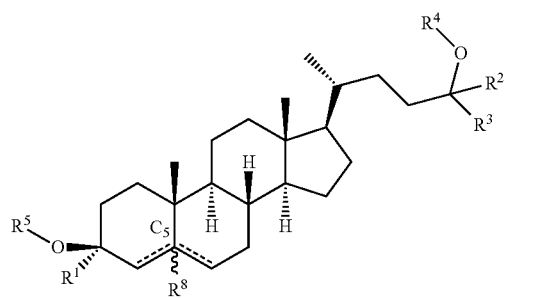

3 Claims, No Drawings

(56) References Cited

U.S. PATENT DOCUMENTS

| | | |
|---|---|---|
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani et al. |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Martinez Botella et al. |
| 2018/0371009 A1 | 12/2018 | Pellicciari et al. |
| 2019/0160078 A1 | 5/2019 | Masuoka et al. |

FOREIGN PATENT DOCUMENTS

| | | |
|---|---|---|
| WO | 0211708 A2 | 2/2002 |
| WO | 02053577 A2 | 7/2002 |
| WO | 2002079221 A2 | 10/2002 |
| WO | 2003039480 A2 | 5/2003 |
| WO | 03049685 A2 | 6/2003 |
| WO | 2003082893 A2 | 10/2003 |
| WO | 2004055201 A2 | 7/2004 |
| WO | 2005079810 A1 | 9/2005 |
| WO | 2009059961 A2 | 5/2009 |
| WO | 2009090063 A1 | 7/2009 |
| WO | 2010075282 A1 | 7/2010 |
| WO | 2010088414 A2 | 8/2010 |
| WO | 2011014661 A2 | 2/2011 |
| WO | 2011028794 A2 | 3/2011 |
| WO | 2011067501 A1 | 6/2011 |
| WO | 2012064501 A1 | 5/2012 |
| WO | 2012142039 A1 | 10/2012 |
| WO | 2013019711 A2 | 2/2013 |
| WO | 2013036835 A1 | 3/2013 |
| WO | 2013056181 A1 | 4/2013 |
| WO | 2013163455 A2 | 10/2013 |
| WO | 2014028942 A2 | 2/2014 |
| WO | 2014115167 A2 | 7/2014 |
| WO | 2014120786 A1 | 8/2014 |
| WO | 2014160441 A1 | 10/2014 |
| WO | 2014160480 A1 | 10/2014 |
| WO | 2015195967 A1 | 12/2015 |
| WO | 2016007762 A1 | 1/2016 |
| WO | 2016057713 A1 | 4/2016 |
| WO | 2017007832 A1 | 1/2017 |
| WO | 2017007836 A1 | 1/2017 |
| WO | 2017007840 A1 | 1/2017 |
| WO | 2017037465 A1 | 3/2017 |
| WO | 2018170336 A1 | 9/2018 |

OTHER PUBLICATIONS

Pubchem, CID 66966798, pp. 1-3.
Pubchem, CID 70604305, pp. 1-3.
Pubchem, CID 71508953, pp. 1-13.
Reddy, "Pharmacology of endogenous neuroactive steroids, Crit Rev Neurobiol", 2003;15(3-4) pp. 197-234.
Schmidt et al., "Inhibitory effect of oxygenated cholestan-3b-ol derivatives on the growth of Mycobacterium tuberculosis", Bioorganic & Medicinal Chemistry Letters, vol. 23, No. 22, (2013), pp. 6111-6113.
Stamp et al., "Plasma Levels and Therapeutic Effect of 25-Hydroxycholecalciferol in Epileptic Patients taking Anticonvulsant Drugs", British Medical Journal, vol. 4, 1972, pp. 9-12.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Steinrauf et al., "Synthesis and Evaluation of Sulfur-Containing Steroids Against Methylmercuric Chloride Toxicity", Journal of Pharmaceutical Sciences, vol. 67, No. 12, pp. 1739-1743, (1978).
Takano et al., "Simple Synthesis of 3b, 24-Dihydroxychol-5-EN-7-ONE by Oxidative Cleavage of the Side Chain of Cholesterol", Chemistry Letters, vol. 14, No. 8, (1985), pp. 1265-1266.
Tierney et al., " Abnormalities of Cholesterol Metabolism in Autism Spectrum Disorders", Am J Med Genet B Neuropsychiatr Genet. vol. 1418, No. 6, (2006), pp. 666-668_.
Vincent Chen et al., "The chemical biology of clinicall tolerated NMDA receptor antagonists", Journal of Neurochemistry, (2006), pp. 1611-1626.
Wolozin et al., "The Cellular Biochemistry of Cholesterol and Statins: Insights into the Pathophysiology and Therapy of Alzheimer's Disease" vol. 10, No. 2, 2004, pp. 127-146.
Wong et al., An efficient and convenient transformation of a-haloketones to a-hydroxyketones using cesium formate. Journal of Organometallic Chemistry 2006, 694, 3452-3455.
Xilouri et al., "Neuroprotective effects of steroid analogues on P19-N neurons", Neurochemistry International, (2007), vol. 50, No. 4, pp. 660-670.
Yang et al., "New cytotoxic oxygenated sterols from marine bryozoan Bugula neritina", Natural Product Research, vol. 25, No. 16, (2011), pp. 1505-1511.
Yoon-Seok et al., "Neuroprotective Effects of Ginsenoside Rg3 against 24-0H-cholesterol-induced Cytotoxicity in Cortical Neurons", Journal of Ginseng Research, vol. 34, No. 3, pp. 246-253, (2010).
Zuliani et al., "Plasma 24S-hydroxycholesterol levels in elderly subjects with late onset Alzheimer's disease or vascular lementia: a case-control study" BMC Neurology, vol. 11, No. 121, pp. 1-8, (2011).
Cecil Textbook of Medicine, 20th edition (1996), vol. 2, pp. 1992-1996.
Cecil Textbook of Medicine, 20th edition (1996), vol. 2, pp. 2050-2057.
Citraro et al., "Effects of some neurosteroids injected into some brain areas of WAG/Rij rats, an animal model of generalized absence epilepsy", Neuropharmacology, (2006), vol. 50, No. 8, pp. 1059-1071.
Collingridge, "The NMDA receptor as a target for cognitive enhancement", Neuropharmacology. (2013), pp. 13-26, abstract.
Connick et al., "Program No. 613 1/B86", 2009 Neuroscience Meeting Planner. Chicago, IL: Society for Neuroscience, (2009).
Corman et al., "Structure-Activity Relationships for Side Chain Oxysterol Agonists of the Hedgehog Signaling Pathway", ACS Medicinal Chemistry Letters, Aug. 28, 2012, 3, 828-833.
Cross et al., "Steroids CCLXXIN 1. Biologically-Active Labile Ethers IV2. The Synthesis of 22-Oxa-25-Azacholesterol and Related Compounds", Steroids, Elsevier Science Publishers, vol. 5, No. 5, pp. 585-598, (1965).
Database Chemical Abstracts Service, Xiangdong et al. "Highly stereoselective synthesis of 24R,25- and 24S, 25-dihydroxysteroid", Database acession No. 2001:174431, (2000).
Dayal et al., "Stereospecific synthesis of 3b-hydroxylated bile alcohols", Journal of Lipid Research, vol. 25, No. 6, (1984), pp. 646-650.
Extended European Search Report for Application No. 15809462.3 dated Nov. 29, 2017.
Extended European Search Report for European Application No. 14775126.7.
Extended European Search Report for European Application No. 15849514.3 dated May 23, 2018.
Extended European Search Report for PCTUS2014/026784 dated Aug. 17, 2016.

(56) References Cited

OTHER PUBLICATIONS

FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.
Festa et al., "Exploitation of Cholane Scaffold for the Discovery of Potent and Selective Farnesoid X Receptor (FXR) and G-Protein Coupled Bile Acid Receptor 1 (GP-BAR1) Ligands", Journal of Medicinal Chemistry, vol. 57, No. 20, (2014), pp. 8477-8495.
Foster et al., "Effect of steroids on 13-adrenoceptor-mediated relaxation of pig bronchus", Br. J. Pharmac. vol. 78, 1983, pp. 441-445.
Gunatilaka et al., "Bioactive Ergost-5-ENE-3b, 7a-DIOL Derivatives from Pseudobersama Mossambicensis", Journal of Natural Products, vol. 55, No. 11, (1992), pp. 1648-1654.
Hoffmeister et al., "Zur Chemie des Ecdysons, III: Vergleichende spektrometrische Untersuchungen an a.b-ungesättigten Steroidketonen", Chemische Berichte, (1965), vol. 98, pp. 2361-2375.
International Search Report and Written Opinion for corresponding International Application No. PCT/US14/26633 dated Jul. 14, 2014.
International Search Report and Written Opinion for corresponding International Application No. PCT/US15/36510 dated Sep. 15, 2015.
International Search Report and Written Opinion for corresponding International Application No. PCT/US17/25535 dated Jul. 3, 2017.
International Search Report and Written Opinion for corresponding International Application No. PCT/US17/31374 dated Jul. 17, 2017.
International Search Report and Written Opinion for corresponding International Application No. PCT/US2012/054261 dated Nov. 28, 2012.
International Search Report and Written Opinion for corresponding International Application No. PCT/US2014/026784 dated Jul. 8, 2014.
International Search Report and Written Opinion for corresponding International Application No. PCT/US2015/054551 dated Jan. 8, 2016.
International Search Report and Written Opinion for corresponding International Application No. PCT/US2016/041160 dated Oct. 28, 2016.
International Search Report and Written Opinion for corresponding International Application No. PCT/US2016/041168 dated Sep. 15, 2016.
International Search Report and Written Opinion for corresponding International Application No. PCT/US2016/041175 dated Sep. 16, 2016.
International Search Report and Written Opinion for corresponding International Application No. PCT/US2017/041199 dated Aug. 29, 2017.
International Search Report and Written Opinion for corresponding International Application No. PCT/US2017/054657 dated Nov. 21, 2017.
International Search Report and Written Opinion for corresponding International Application No. PCT/US2017/057276 dated Nov. 12, 2017.
International Search Report and Written Opinion for corresponding International Application No. PCT/US2017/057277 dated Feb. 20, 2018.
Karaki et al., "Structure-activity relationship studies of Niemann-Pick type C1-like 1 (NPC1L1) ligands identified by screening assay monitoring pharmacological chaperone effect", Bioorganic & Medicinal Chemistry, vol. 21, Issue 17, (2013), pp. 5297-5309.
Khripach et al., "Synthesis of (24S)-Hydroxy-and (24S)-24,25-Epoxycholesterol Analogues, Potential Agonists of Nuclear LXR Receptors", Russian Journal of Bioorganic Chemistry, Kluwer Academic Publishers-Plenum Publishers, NE, vol. 32, No. 6, pp. 586-594, (2006).
<Kurosawa et al., "Synthesis of 19-Hydroxylated Bile Acids and Identification of 3a,7a,12a,19-Tetrahydroxy-5b-cholan-24oic Acid in Human Neonatal Urine" 1995, Chem. Pharm. Bull, vol. 43, No. 9, pp. 1551-1557.

Leoni et al., "Oxysterols as biomarkers in neurodegenerative diseases", Chemistry and Physics of Lipids, vol. 164 (2011), pp. 515-524.
Lettré, et al., "Mehrwertige Alkohole aus Sterinen und Sterinderivaten, VI Steroide mit Strukturmerkmalen des Ecdysons und der Elatericine", Justus Liebigs Annalen der Chemie, (1972), vol. 758, pp. 89-110. English Abstract.
Li et al., "Synthesis of 7a-hydroxy derivatives of regulatory oxysterols", Steroids, vol. 65, No. 9, (2000), pp. 529-535.
Mouriño et al., "Studies on vitamin D (calciferol) and its analogs. 15.24-Nor-1a.,25-dihydroxyvitamin D3 and 24-nor-25-hydroxy-5,6-trans-vitamin D3", J. Med. Chem., (1978), vol. 21, No. 10, pp. 1025-1029.
Nagano et al., "Chemistry and Biochemistry of Chinese Drugs. Part II. Hydroxylated Sterols, Cytotoxic Towards cancerous Cells: Synthesis and Testing", Journal of Chemical Research, vol. 9, pp. 218 (1977).
Olkkonen et al., "Oxysterols and Their Cellular Effectors", Biomolecules, vol. 2 (2012), pp. 76-103.
Park-Chung et al., "Distinct sites for inverse modulation of N-methyl-D-aspartate receptors by sulfated steroids", Molecular Pharmacology, vol. 52, No. 6, (1997), pp. 1113-1123.
Partial International Search Report and Provisional Opinion for corresponding Internation Application No. PCT/ US2017/057277 dated Dec. 20, 2017.
Partial Supplementary European Search Report for European Application No. 14775126.7 dated Sep. 14, 2016.
Paul et al., "The Major Brain Cholesterol Metabolite 24 (S)—Hydroxycholesterol Is a Potent Allosteric Modulator of N-Methyl-D-Aspartate Receptors", Journal of Neuroscience, vol. 33, No. 44, pp. 17290-17300, (2013).
Pubchem, 25-Hydroxycholesterol, CID 65094, pp. 1-6.
Pubchem, CID 132021, pp. 1-15.
Pubchem, CID 54083335, pp. 1-3.
Pubchem, CID 54160779, pp. 1-3.
Pubchem, CID 58455549, pp. 1-4.
Bukelis et al., "Smith-Lemli-Opitz Syndrome and Autism Spectrum Disorder", American Journal of Psychiatry, 2007, vol. 164, pp. 1655-1661.
Cook et al., "24-hydroxycholesterol sulfation by human cytosolic sulfotransferases: Formation of monosulfates and disulfates, molecular modeling, sulfatase sensitivity, and inhibition of liver x receptor activation", Drug Metabolism and Disposition, vol. 37, No. 10, (2009), pp. 2069-2078.
Extended European Search Report for Application No. 16821920.2 dated Jan. 31, 2019.
Extended European Search Report for Application No. 16821924.4 dated Jan. 31, 2019.
Extended European Search Report for Application No. 16821926.9 dated Jan. 31, 2019.
Knoppert et al., "Position Paper: Paediatric Age Categories to be Used in Differentiating Between Listing on a Model Essential Medicines List for Children", 2007, pp. 1-5.
Linsenbardt et al., "Different oxysterols have opposing actionss at N-methyl-d-aspartate receptors", Neuropharmacology., vol. 85 (2014), pp. 232-242.
Mateos et al., "Activity-regulated cytoskeleton-associated protein in rodent brain is down regulated by high fat diet in vivo and by 27-hydroxycholesterol in vitro", Brain Pathology. vol. 19, No. 1, (2009), pp. 69-80.
Sepe et al., "Total Synthesis and Pharmacological Characterization of Solomonsterol A, a Potent Marine Pregnane-X-Receptor Agonist Endowed with Anti-Inflammatory Activity", Journal of Medicinal Chemistry, vol. 54, (2011), pp. 4590.
Tomek et al., "NMDA Receptor Modulators in the Treatment of Drug Addiction", Pharmaceuticals (Basel), 2013, vol. 6, No. 2, pp. 251-258.
Yan et al., "Characterization of a synthetic steroid 24-keto-cholest-5-en-3b, 19-diol as a neuroprotectant", CNS Neuroscience & Therapeutics, vol. 21, No. 6, (2015), pp. 486-495.

(56) References Cited

OTHER PUBLICATIONS

Björkhem et al., "Oxysterols in the circulation of patients with the Smith-Lemli-Opitz syndrome: abnormal levels of 24S-and 27-hydroxycholesterol", Journal of Lipid Research, vol. 42, 2001, pp. 366-371.
Cancer [online], [retrieved on Jul. 6, 2007]. Retrieved from the internet, URL http://www.nlm.nih.gov/medlineplus/cancer.html>.
Golub et al., "Molecular classification of cancer: Class discovery and class prediction by gene expression monitoring", Science (1999), vol. 286, pp. 531-537.
Lala et al., "Role of nitric oxide in tumor progression: Lessons from experimental tumors", Cancer and Metastasis Reviews, (1998), 17 (1), pp. 91-106.
Luu et al., "Oxysterols: Old Tale, New Twists", Annual Reviews. Pharmacol. Toxicol. (2016), vol. 56, pp. 447-467.
Svoboda et al. (Am J Med Genet C Semin Med Genet (2012), pp. 285-294) (Year: 2012).

\* cited by examiner

OXYSTEROLS AND METHODS OF USE THEREOF

RELATED APPLICATIONS

The present application is a U.S. National Phase Application under 35 U.S.C. § 371 of International Application No. PCT/US2016/041160, filed Jul. 6, 2016, which claims the benefit of and priority to U.S. Provisional Application No. 62/189,065 filed Jul. 6, 2015, the contents of each of which are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are derived from cholesterol and have been shown to potently and selectively modulate NMDA receptor function. New and improved oxysterols are needed that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols. Further provided are pharmaceutical compositions comprising the compounds of the present invention, and methods of their use and treatment.

Compounds described herein may, in certain embodiments, behave as "pro-drugs," or compounds that are metabolized (e.g., hydrolyzed) in vivo to more active compounds (e.g., into a pharmaceutically active therapeutic agent). A review of pro-drugs and their design can be found in Huttunen et al., Pharmacol. Rev. 2011, 63: 750-771, the contents of which are incorporated herein in its entirety. In some embodiments, the compounds described herein have improved physical properties (e.g., improved solubility) as compared to their metabolized (e.g., hydrolyzed) compound product. In some embodiments, the compounds described herein have improved bioavailability or absorption in the body.

In one aspect, provided herein are compounds according to Formula (I):

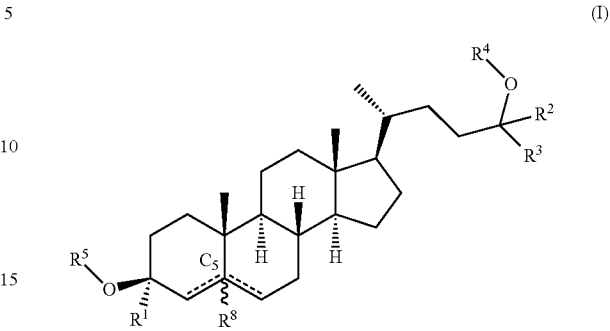

(I)

or a pharmaceutically acceptable salt thereof, wherein: $R^1$ is hydrogen or $C_{1-6}$ alkyl; each of $R^2$ and $R^3$ is independently hydrogen, $C_{1-6}$ alkyl, carbocyclyl, or heterocyclyl; or $R^2$ and $R^3$, together with the carbon atom to which they are attached, form a 3-8 membered ring (e.g., 3-8 membered carbocyclyl or heterocyclyl ring); each of $R^4$ and $R^5$ is independently hydrogen; R is absent or hydrogen; ==== represents a single or double bond, wherein when one ==== is a double bond, the other ==== is a single bond and $R^8$ is absent; and at least one hydrogen is replaced by a moiety cleavable under biological conditions.

In some embodiments, the compound of Formula (I) is a compound of Formula (I-AA):

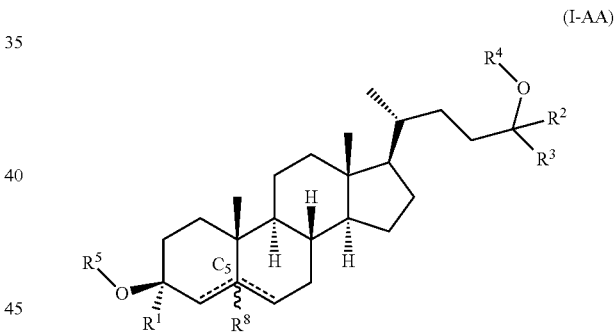

(I-AA)

or a pharmaceutically acceptable salt thereof, wherein: $R^1$ is hydrogen or $C_{1-6}$ alkyl; each of $R^2$ and $R^3$ is independently hydrogen, $C_{1-6}$ alkyl, carbocyclyl, or heterocyclyl; or $R^2$ and $R^3$, together with the carbon atom to which they are attached, form a 3-8 membered ring (e.g., 3-8 membered carbocyclyl or heterocyclyl ring); each of $R^4$ and $R^5$ is independently hydrogen or a moiety cleavable under biological conditions; $R^8$ is absent or hydrogen; and ==== represents a single or double bond, wherein when one ==== is a double bond, the other ==== is a single bond and $R^8$ is absent.

In some embodiments, $R^4$ and $R^5$ are not both hydrogen.
In some embodiments, $R^4$ is not hydrogen. In some embodiments, $R^4$ is not hydrogen and $R^5$ is hydrogen.
In some embodiments, $R^5$ is not hydrogen.
In some embodiments, each of $R^4$ and $R^5$ is independently hydrogen, —P(O)($R^a$)$_2$, —S(O)$_x$$R^b$, —C(O)$R^c$, —C(O)N($R^d$)$_2$, —(CH$_2$)$_x$C(O)N($R^d$)$_2$, —C(O)O$R^c$, —(CH$_2$)$_n$OP(O)($R^a$)$_2$, —(CH$_2$)$_m$OS(O)$_x$$R^b$, —(CH$_2$)$_p$OC(O)$R^c$, or —(CH$_2$)$_p$C(O)O$R^c$; each of $R^a$ and $R^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4. In some embodiments, each of R$^4$ and R$^5$ is independently —C(O)R$^c$, wherein R$^c$ is an amino acid (e.g., glycine, alanine, valine). In some embodiments, each of R$^4$ and R$^5$ is independently an amino acid ester.

In some embodiments, R$^4$ is hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, R$^1$ is C$_{1-6}$ alkyl (e.g., substituted or unsubstituted C$_{1-6}$ alkyl). In some embodiments, R$^1$ is hydrogen. In some embodiments, R$^1$ is hydrogen, methyl (e.g., —CH$_3$, —CF$_3$ or —CH$_2$OCH$_3$), ethyl, or isopropyl. In some embodiments, R$^1$ is methyl or ethyl.

In some embodiments, each of R$^2$ and R$^3$ is independently hydrogen, methyl (e.g., —CH$_3$, —CF$_3$) ethyl, isopropyl, cyclopropyl, or butyl.

In some embodiments, R$^4$ is a moiety cleavable under biological conditions and R$^5$ is hydrogen.

In some embodiments, R$^4$ is hydrogen and R$^5$ is a moiety cleavable under biological conditions. In some embodiments, each of R$^4$ and R$^5$ is a moiety cleavable under biological conditions. In some embodiments, each of R$^4$ and R$^5$ is independently hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, (CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, R$^4$ is hydrogen, R$^5$ is —S(O)$_x$R$^b$, x is 2, and R$^b$ is not —OH. In some embodiments, not both of R$^4$ or R$^5$ are hydrogen.

In some embodiments, R$^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; R$^5$ is hydrogen; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4. In some embodiments, R$^4$ is hydrogen; R$^5$ is —P(O)(R$^a$)$_2$, —S(O)$_x$R$^b$, —C(O)R$^c$, —C(O)N(R$^d$)$_2$, —(CH$_2$)C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; each of n, m, p is independently 1, 2, 3, or 4; wherein when R$^5$ is —S(O)$_x$R$^b$ and x is 2, R$^b$ is not —OH. In some embodiments, R$^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, each of R$^a$ and R$^b$ is independently —OR$^d$, R$^d$ is hydrogen or alkyl, and x is 2. In some embodiments, R$^c$ is alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); and R$^d$ is hydrogen or alkyl (e.g., methyl (e.g., —CH$_3$)).

In some embodiments, each of n, m, and p is independently 1 or 2.

In some embodiments, R$^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, R$^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, each of R$^a$ and R$^b$ is independently —OR$^d$, R$^d$ is hydrogen or alkyl, and x is 2. In some embodiments, R$^c$ is alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); and R$^d$ is hydrogen or alkyl (e.g., methyl (e.g., —CH$_3$)). In some embodiments, each of n, m, and p is independently 1 or 2. In some embodiments, R$^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, R$^4$ is hydrogen, and R$^5$ is not —S(O)$_2$OH.

In some embodiments, each of ==== is a single bond.

In some embodiments, the compound of Formula (I) is a compound of Formula (I-A) or Formula (I-B):

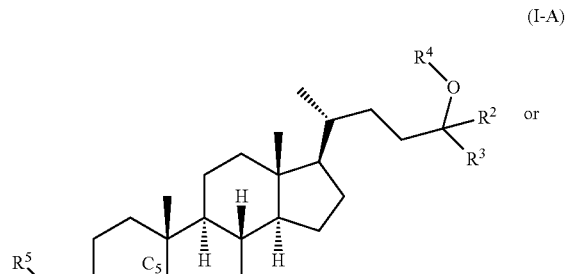

(I-A)

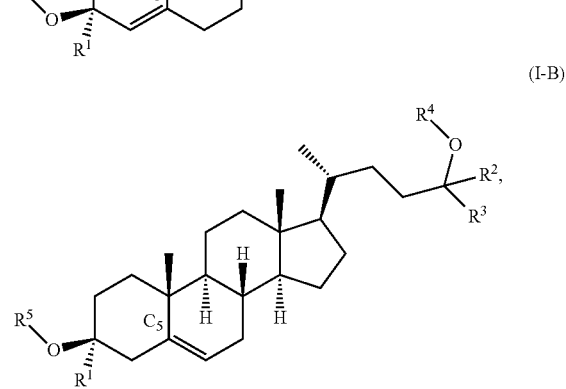

(I-B)

or a pharmaceutically acceptable salt thereof.

In some embodiments, the compound of Formula (I) is a compound of Formula (I-B):

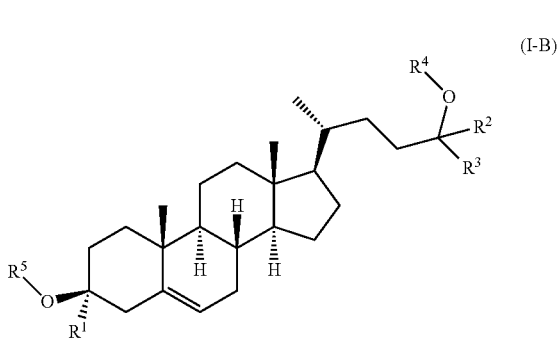

(I-B)

or a pharmaceutically acceptable salt thereof.

In some embodiments, $R^1$ is alkyl (e.g., substituted or unsubstituted alkyl). In some embodiments, $R^1$ is hydrogen. In some embodiments, $R^1$ is hydrogen, methyl (e.g., —CH$_3$, —CF$_3$ or —CH$_2$OCH$_3$), ethyl, or isopropyl.

In some embodiments, each of $R^2$ and $R^3$ is independently hydrogen, methyl (e.g., —CH$_3$, —CF$_3$), ethyl, isopropyl, cyclopropyl, or butyl.

In some embodiments, $R^4$ is a moiety cleavable under biological conditions and $R^5$ is hydrogen. In some embodiments, $R^4$ is hydrogen and $R^5$ is a moiety cleavable under biological conditions.

In some embodiments, each of $R^4$ and $R^5$ is a moiety cleavable under biological conditions. In some embodiments, each of $R^4$ and $R^5$ is independently hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., unsubstituted alkyl or substituted alkyl, e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4, wherein when $R^4$ is hydrogen and $R^5$ is —S(O)$_x$R$^b$ and x is 2, R$^b$ is not —OH.

In some embodiments, not both of $R^4$ and $R^5$ are hydrogen.

In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; $R^5$ is hydrogen; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, $R^4$ is hydrogen; $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each of n, m, p is independently 1, 2, 3, or 4; wherein when $R^5$ is —S(O)$_x$R$^b$ and x is 2, R$^b$ is not —OH. In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, when $R^4$ is hydrogen, $R^5$ is not —S(O)$_2$OH.

In some embodiments, the compound of Formula (I-B) is a compound of Formula (I-C):

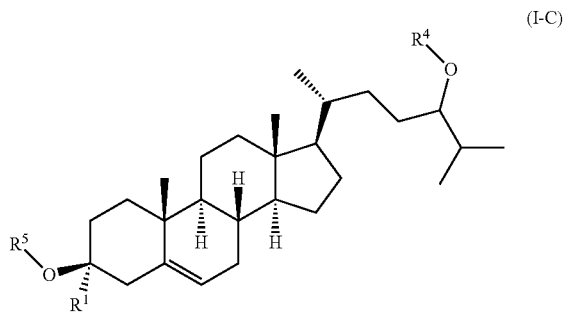

(I-C)

or a pharmaceutically acceptable salt thereof.

In some embodiments, $R^1$ is hydrogen, methyl (e.g., —CH$_3$, —CF$_3$, —CH$_2$OCH$_3$), ethyl, or isopropyl. In some embodiments, $R^1$ is methyl or ethyl.

In some embodiments, $R^4$ is a moiety cleavable under biological conditions and $R^5$ is hydrogen. In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue. In some embodiments, $R^4$ is hydrogen and $R^5$ is a moiety cleavable under biological conditions.

In some embodiments, $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, each of $R^4$ and $R^5$ is a moiety cleavable under biological conditions.

In some embodiments, $R^1$ is alkyl (e.g., substituted or unsubstituted alkyl).

In some embodiments, $R^1$ is hydrogen, and when $R^4$ is hydrogen, then $R^5$ is not —S(O)$_2$OH. In some embodiments, $R^1$ is hydrogen, and when $R^4$ is hydrogen, then $R^5$ is —P(O)(R$^a$)$_2$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$. In some embodiments, $R^1$ and $R^5$ are hydrogen. In some embodiments, $R^1$ is hydrogen and $R^5$ is not —S(O)$_2$OH. In some embodiments, $R^1$ is hydrogen and $R^5$ is —P(O)(R$^a$)$_2$, —C(O)R$^c$, —C(O)N(R$^d$)$_2$, —(CH$_2$)$_x$C(O)N(R$^d$)$_2$, —C(O)

OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$.
In some embodiments, the compound of Formula (I-C) is a compound of Formula (I-D):
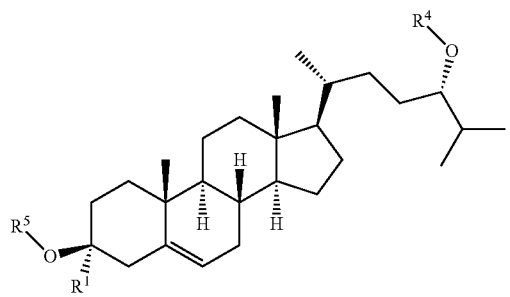
or a pharmaceutically acceptable salt thereof.
In some embodiments, the compound is selected from the group consisting of:
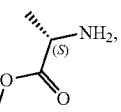
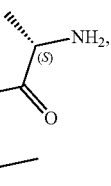
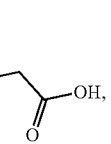
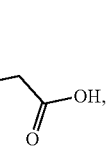
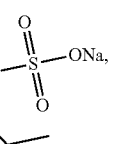

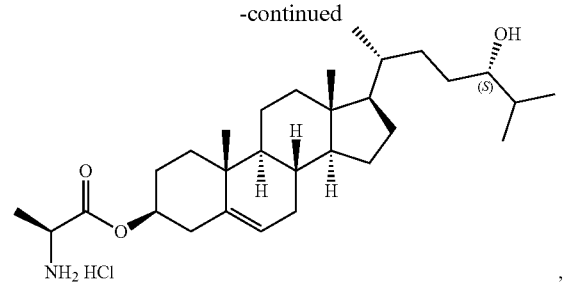
,
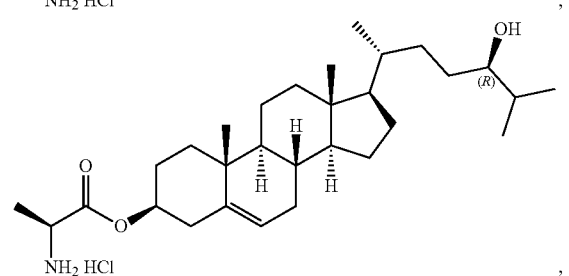
,
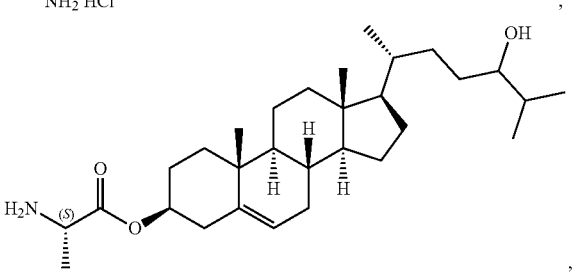
,
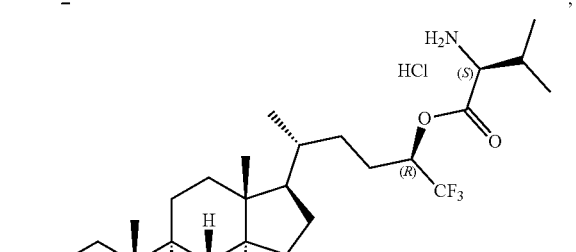
,
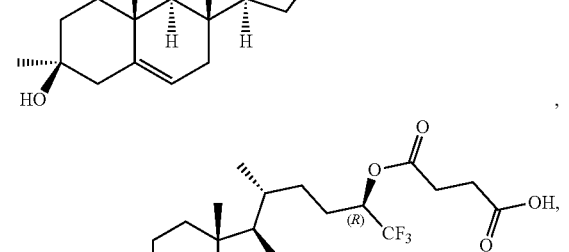
,
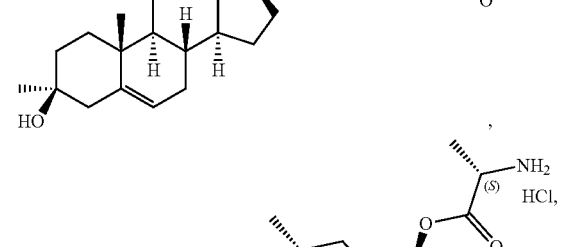
,
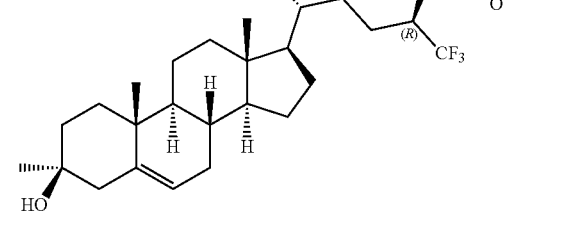
,
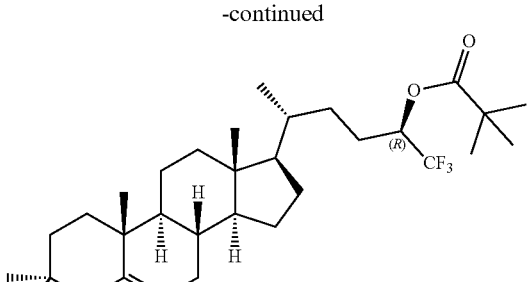
,
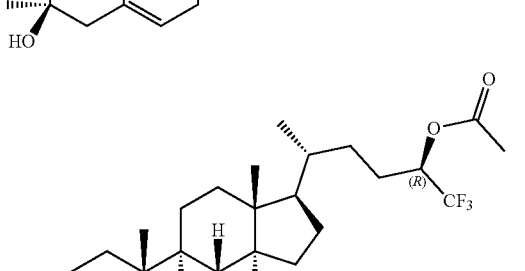
,
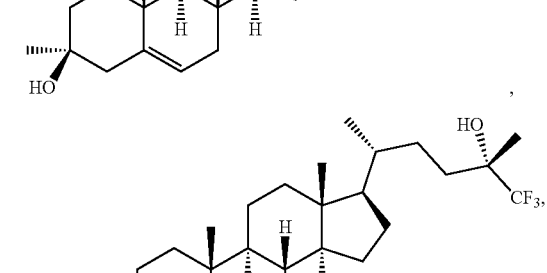
,
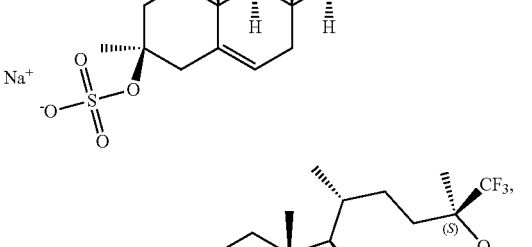
,
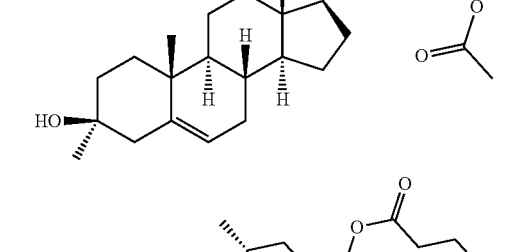
,
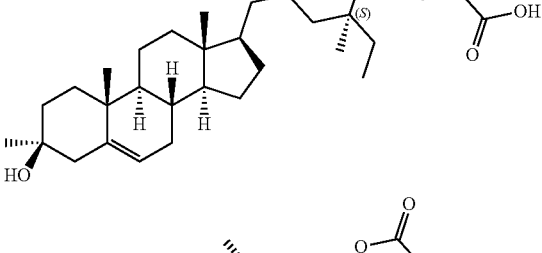
,
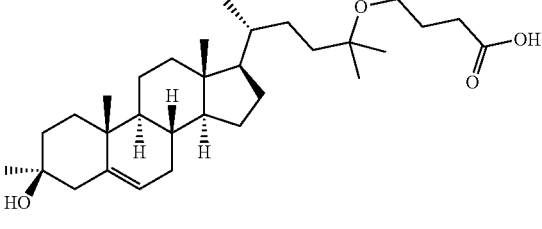
, -continued

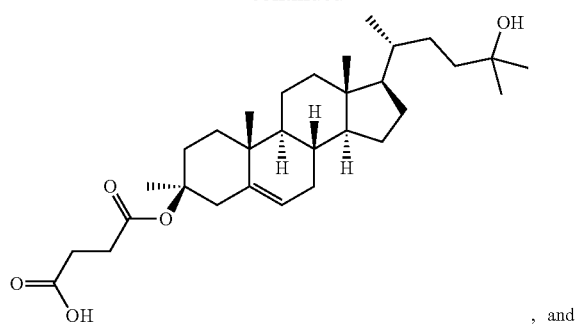

, and

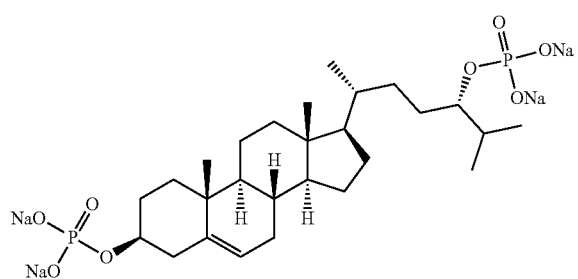

or a pharmaceutically acceptable salt thereof.

In some embodiments, the compound is selected from the group consisting of:

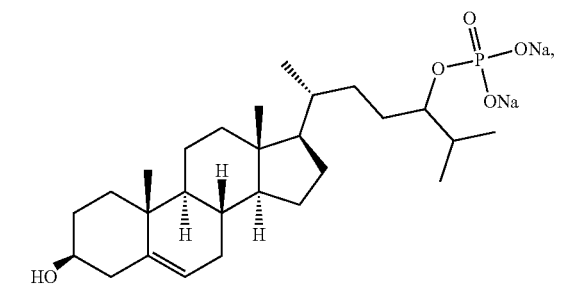

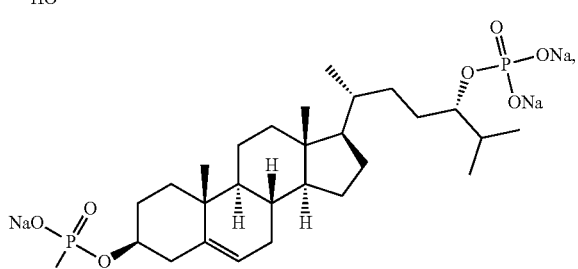

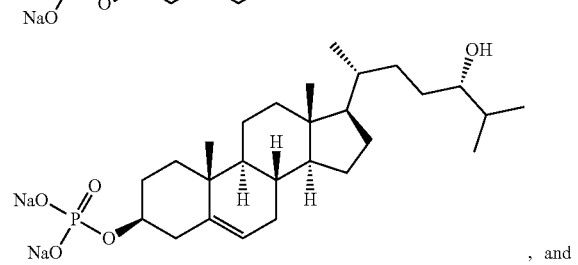

, and

-continued

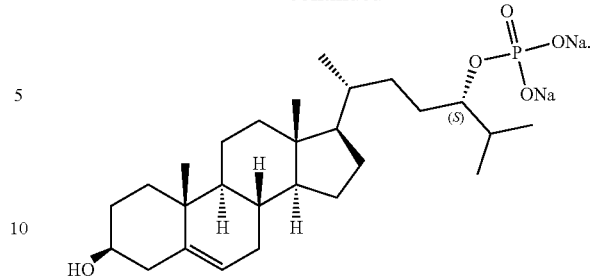

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a metabolic disorder.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia (e.g., frontotemporal dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain; headaches, e.g., migraine headaches), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

In some embodiments, the disorder is Huntington's disease. In some embodiments, the disorder is Parkinson's disease. In some embodiments, the disorder is an inflammatory disease (e.g., lupus).

In some embodiments, the disorder is sterol synthesis disorder.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —CH$_3$). In certain embodiments, the alkyl group is substituted $C_{1-10}$ alkyl. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethylene (—C(CH$_3$)=CH—, —CH=C(CH$_3$)—), substituted propylene (e.g., —C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

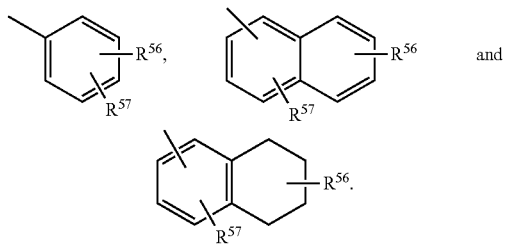

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

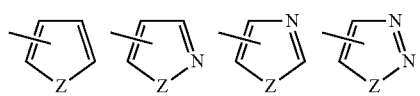

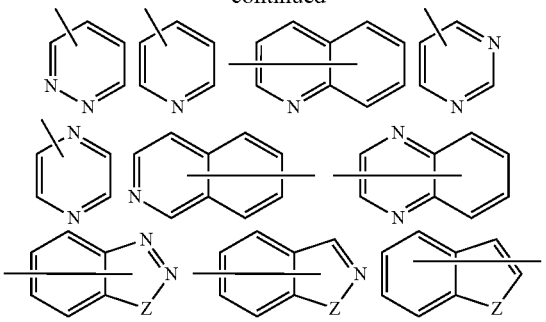

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_3$ 8 carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstitued alkenyl, substituted or unsubstituted alkynyl, substituted or unsubstitued carbocyclyl, substituted or unsubstituted heterocyclyl, substituted or unsubstituted aryl, or substituted or unsubstitued heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethyl-butoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both R$^{38}$ groups are joined to form an alkylene group.

Exemplary "substituted amino" groups include, but are not limited to, —NR$^{39}$—$C_1$-$C_8$ alkyl, —NR$^{39}$—(CH$_2$)$_t$($C_6$-$C_{10}$ aryl), —NR$^{39}$—(CH$_2$)$_t$(5-10 membered heteroaryl), —NR$^{39}$—(CH$_2$)$_t$($C_3$-$C_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R, —SO$_2$N(R$^{bb}$)$_2$, —SO$_2$R$^{aa}$, —SO$_2$OR$^{aa}$, —OSO$_2$R, —S(=O)R$^{aa}$, —OS(=O)R$^{aa}$, —Si(R$^{aa}$)$_3$, —OSi(R$^{aa}$)$_3$ —C =S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R, —OP(=O)$_2$R, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^a$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^{aa}$)$_2$, —P(=O)$_2$N(R$^{cc}$)$_2$, —P(=O)$_2$(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NRCO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^e$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;
each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups; each instance of R$^{ff}$ is, independently, selected from hydrogen, C$_{1-6}$ alkyl, C$_{1-6}$ perhaloalkyl, C$_2$-alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-4}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, C$^-$, Br$^-$, Br$^-$, I$^-$), NO$_3$$^-$, ClO$_4$$^-$, OH$^-$, H$_2$PO$_4$$^-$, HSO$_4$$^-$, SO$_4$$^{-2}$sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^a$, —SO$_2$R$^{aa}$, —C(=NR$^{bb}$)R$^a$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, and unless otherwise specified, a "moiety cleavable under biological conditions" refers to a moiety that is released (e.g., hydrolytically, enzymatically) in vivo or in vitro. For example, a moiety cleavable under biological conditions is an ester, phosphate, or sulfate. In some embodiments, a moiety cleavable under biological conditions is $-P(O)(R^a)_2$, $-S(O)_xR^b$, $-C(O)R^c$, $-C(O)N(R^d)_2$, $-(CH_2)_xC(O)N(R^d)_2$, $-C(O)OR^c$, $-(CH_2)_nOP(O)(R^a)_2$, $-(CH_2)_mOS(O)_xR^b$, $-(CH_2)_pOC(O)R^c$, or $-(CH_2)_pC(O)OR^c$; each of $R^a$ and $R^b$ is independently selected from $-OR^d$ or alkyl; each $R^c$ is independently alkyl (e.g., $-CH_2NH_2$, $-CH_2CH_2CO_2H$, $-CH(CH(CH_3)_2)NH_2$, $-CH_2CH_2C(O)OH$, or $-CH(CH_3)NH_2$); each $R^d$ is independently hydrogen or alkyl; each x is independently 1 or 2; and each of n, m, p is independently 1, 2, 3, or 4.

Detailed Description of Certain Embodiments of the Invention

[1] As generally described herein, the present invention provides oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

[2] The compounds described herein comprise a moiety cleavable under biological conditions, for example by enzymes (e.g., hydrolases).

Compounds

In one aspect, provided herein are compounded according to Formula (I):

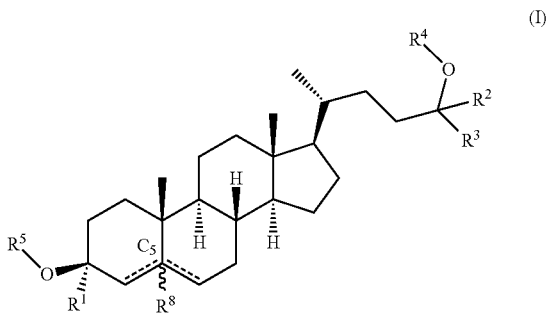

(I)

or a pharmaceutically acceptable salt thereof, wherein: R is hydrogen or $C_{1-6}$ alkyl; each of $R^2$ and $R^3$ is independently hydrogen, $C_{1-6}$ alkyl, or carbocyclyl, or $R^2$ and $R^3$, together with the carbon atom to which they are attached, form a 3-8 membered ring; each of $R^4$ and $R^5$ is independently hydrogen; $R^8$ is absent or hydrogen; ==== represents a single or double bond, wherein when one ==== is a double bond, the other ==== is a single bond and $R^8$ is absent; and at least one hydrogen is replaced by a moiety cleavable under biological conditions.

In some embodiments, the compound of Formula (I) is a compound of Formula (I-AA):

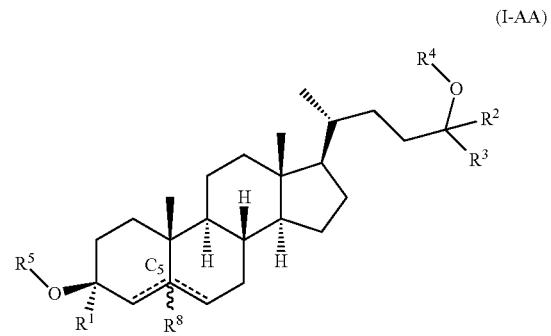

(I-AA)

or a pharmaceutically acceptable salt thereof, wherein: $R^1$ is hydrogen or $C_{1-6}$ alkyl; each of $R^2$ and $R^3$ is independently hydrogen, $C_{1-6}$ alkyl, or carbocyclyl, or $R^2$ and $R^3$, together with the carbon atom to which they are attached, form a 3-8 membered ring; each of $R^4$ and $R^5$ is independently hydrogen or a moiety cleavable under biological conditions; $R^8$ is absent or hydrogen; and ==== represents a single or double bond, wherein when one ==== is a double bond, the other ==== is a single bond and $R^8$ is absent.

In some embodiments, $R^4$ and $R^5$ are not both hydrogen.
In some embodiments, $R^4$ is not hydrogen.
In some embodiments, $R^5$ is not hydrogen.
In some embodiments, each of $R^4$ and $R^5$ is independently hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4. In some embodiments, each of $R^4$ and $R^5$ is independently —C(O)R$^c$, wherein R$^c$ is an amino acid (e.g., glycine, alanine, valine). In some embodiments, each of $R^4$ and $R^5$ is independently an amino acid ester.

In some embodiments, $R^4$ is hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, $R^1$ is $C_{1-6}$ alkyl (e.g., substituted or unsubstituted $C_{1-6}$ alkyl). In some embodiments, $R^1$ is hydrogen. In some embodiments, $R^1$ is hydrogen, methyl (e.g., —CH$_3$, —CF$_3$, —CH$_2$OCH$_3$), ethyl, or isopropyl. In some embodiments, $R^1$ is methyl or ethyl.

In some embodiments, each of $R^2$ and $R^3$ is independently hydrogen, methyl (e.g., —CH$_3$, —CF$_3$), ethyl, isopropyl, cyclopropyl, or butyl.

In some embodiments, $R^4$ is a moiety cleavable under biological conditions and $R^5$ is hydrogen.

In some embodiments, $R^4$ is hydrogen and $R^5$ is a moiety cleavable under biological conditions. In some embodiments, each of $R^4$ and $R^5$ is a moiety cleavable under biological conditions. In some embodiments, each of $R^4$ and $R^5$ is independently hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, when $R^4$ is hydrogen and $R^5$ is —S(O)$_x$R$^b$ and x is 2, R$^b$ is not —OH.

In some embodiments, not both of $R^4$ or $R^5$ are hydrogen.

In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; $R^5$ is hydrogen; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4. In some embodiments, $R^4$ is hydrogen; $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4; wherein when $R^5$ is —S(O)$_x$R$^b$ and x is 2, R$^b$ is not —OH. In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, each of R$^a$ and R$^b$ is independently —OR$^d$, R$^d$ is hydrogen or alkyl, and x is 2. In some embodiments, R$^c$ is alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); and R$^d$ is hydrogen or alkyl (e.g., methyl).

In some embodiments, each of n, m, and p is independently 1 or 2.

In some embodiments, $R^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)OP(O)(R$^a$)$_2$, —(CH$_2$)$_m$OS(O)$_x$R$^b$, or —(CH$_2$)$_p$OC(O)R$^c$. In some embodiments, each of R$^a$ and R$^b$ is independently —OR$^d$, R$^d$ is hydrogen or alkyl, and x is 2. In some embodiments, R$^c$ is alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); and R$^d$ is hydrogen or alkyl (e.g., methyl). In some embodiments, each of n, m, and p is independently 1 or 2. In some embodiments, $R^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, when $R^4$ is hydrogen, $R^5$ is not —S(O)$_2$OH.

In some embodiments, each of ==== is a single bond.

In some embodiments, the compound of Formula (I) is a compound of Formula (I-A) or Formula (I-B):

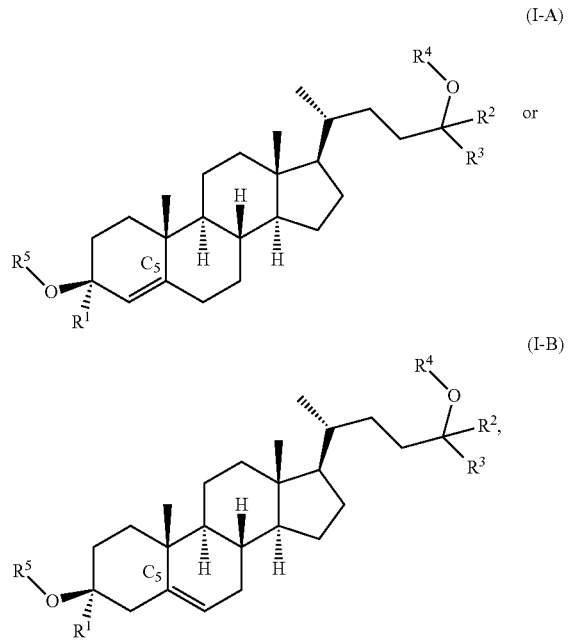

or a pharmaceutically acceptable salt thereof.

In some embodiments, the compound of Formula (I) is a compound of Formula (I-B):

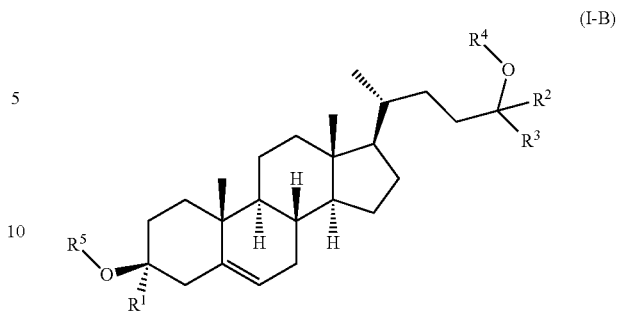

or a pharmaceutically acceptable salt thereof.

In some embodiments, $R^1$ is alkyl (e.g., substituted or unsubstituted alkyl). In some embodiments, $R^1$ is hydrogen. In some embodiments, $R^1$ is hydrogen, methyl (e.g., —CH$_3$, —CF$_3$, —CH$_2$OCH$_3$), ethyl, or isopropyl.

In some embodiments, each of $R^2$ and $R^3$ is independently hydrogen, methyl (e.g., —CH$_3$, —CF$_3$), ethyl, isopropyl, cyclopropyl, or butyl.

In some embodiments, $R^4$ is a moiety cleavable under biological conditions and $R^5$ is hydrogen. In some embodiments, $R^4$ is hydrogen and $R^5$ is a moiety cleavable under biological conditions.

In some embodiments, each of $R^4$ and $R^5$ is a moiety cleavable under biological conditions. In some embodiments, each of $R^4$ and $R^5$ is independently hydrogen, —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., unsubstituted alkyl or substituted alkyl, e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4, wherein when $R^4$ is hydrogen and $R^5$ is —S(O)$_x$R$^b$ and x is 2, R$^b$ is not —OH.

In some embodiments, not both of $R^4$ and $R^5$ are hydrogen.

In some embodiments, $R^4$ is —P(O)(R$^a$)$_2$, —S(O)$_x$R$^b$, —C(O)R$^c$, —C(O)N(R)$_2$, —(CH$_2$)C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$; $R^5$ is hydrogen; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; and each of n, m, p is independently 1, 2, 3, or 4.

In some embodiments, $R^4$ is hydrogen; $R^5$ is —P(O)(R$^a$)$_2$, —S(O)$_x$R$^b$, —C(O)R$^c$, —C(O)N(R$^d$)$_2$, —(CH$_2$)C(O)N(R$^d$)$_2$, —C(O)OR$^c$, —(CH$_2$)$_n$OP(O)(R$^a$)$_2$, —(CH$_2$)$_m$OS(O)R$^b$, —(CH$_2$)$_p$OC(O)R$^c$, or —(CH$_2$)$_p$C(O)OR$^c$; each of R$^a$ and R$^b$ is independently selected from —OR$^d$ or alkyl; each R$^c$ is independently alkyl (e.g., —CH$_2$NH$_2$, —CH$_2$CH$_2$CO$_2$H, —CH(CH(CH$_3$)$_2$)NH$_2$, —CH$_2$CH$_2$C(O)OH, or —CH(CH$_3$)NH$_2$); each R$^d$ is independently hydrogen or alkyl; each x is independently 1 or 2; each of n, m, p is independently 1, 2, 3, or 4; wherein when $R^5$ is —S(O)$_x$R$^b$ and x is 2, R$^b$ is not —OH. In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, when $R^4$ is hydrogen, $R^5$ is not —S(O)$_2$OH.

In some embodiments, the compound of Formula (I-B) is a compound of Formula (I-C):

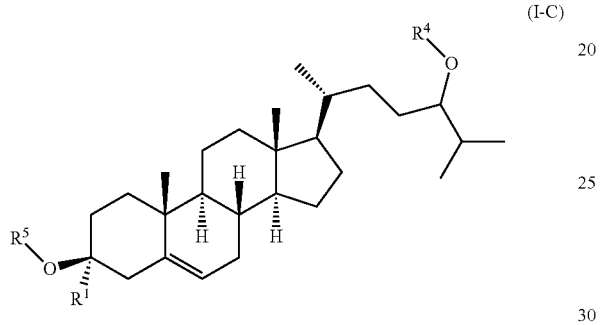

(I-C)

or a pharmaceutically acceptable salt thereof.

In some embodiments, $R^1$ is hydrogen, methyl (e.g., —CH$_3$, —CF$_3$, —CH$_2$OCH$_3$), ethyl, or isopropyl. In some embodiments, $R^1$ is methyl or ethyl.

In some embodiments, $R^4$ is a moiety cleavable under biological conditions and $R^5$ is hydrogen. In some embodiments, $R^4$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^4$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue. In some embodiments, $R^4$ is hydrogen and $R^5$ is a moiety cleavable under biological conditions.

In some embodiments, $R^5$ is —P(O)(R$^a$)$_2$, —S(O)$_x$R$^b$, —C(O)R$^c$, —C(O)N(R$^d$)$_2$, —(CH$_2$)$_x$C(O)N(R$^d$)$_2$, —(CH$_2$)$_n$OP(O)(R$^a$)$_2$, —(CH$_2$)$_m$OS(O)$_x$R$^b$, or —(CH$_2$)$_p$OC(O)R$^c$. In some embodiments, $R^5$ is hydrogen, —P(O)$_2$OH, —S(O)$_2$OH, —CH$_2$OP(O)(OH)$_2$, —C(O)CH$_3$, —C(O)CH$_2$NH$_2$, —C(O)CH$_2$CH$_2$C(O)OH, —C(O)CH(CH(CH$_3$)$_2$)NH$_2$, —C(O)CH(CH$_3$)NH$_2$, or any amino acid residue.

In some embodiments, each of $R^4$ and $R^5$ is a moiety cleavable under biological conditions.

In some embodiments, $R^1$ is alkyl (e.g., substituted or unsubstituted alkyl).

In some embodiments, $R^1$ is hydrogen, and when $R^4$ is hydrogen, then $R^5$ is not —S(O)$_2$OH. In some embodiments, $R^1$ is hydrogen, and when $R^4$ is hydrogen, then $R^5$ is —P(O)(R$^a$)$_2$, —C(O)R$^c$, —C(O)N(R$^d$)$_2$, —(CH$_2$)$_x$C(O)N(R$^d$)$_2$, —C(O)OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$. In some embodiments, $R^1$ and $R^5$ are hydrogen. In some embodiments, $R^1$ is hydrogen and $R^5$ is not —S(O)$_2$OH. In some embodiments, $R^1$ is hydrogen and $R^5$ is —P(O)(R$^a$)$_2$, —C(O)R$^c$, —C(O)N(R$^d$)$_2$, —(CH$_2$)$_x$C(O)N(R$^d$)$_2$, —C(O) OR$^c$, —(CH$_2$)$_n$OP(O)(R$^a$)$_2$, —(CH$_2$)$_m$OS(O)$_x$R$^b$, —(CH$_2$)$_p$OC(O)R$^c$, or —(CH$_2$)$_p$C(O)OR$^c$.

In some embodiments, the compound of Formula (I-C) is a compound of Formula (I-D):

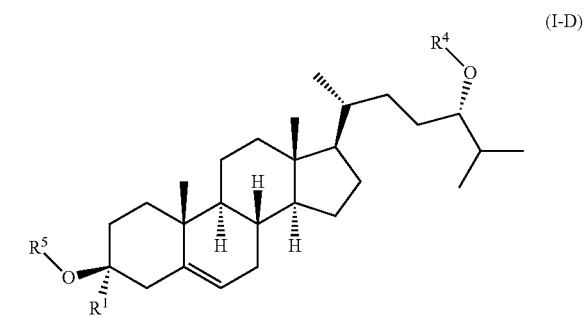

(I-D)

or a pharmaceutically acceptable salt thereof.

In some embodiments, the compound is selected from the group consisting of:

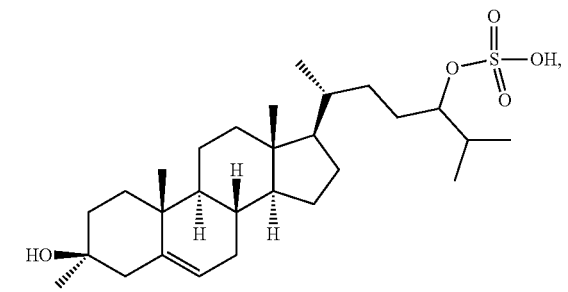

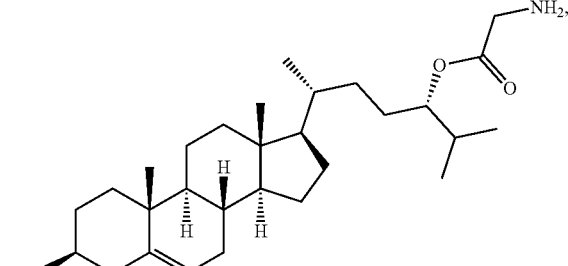

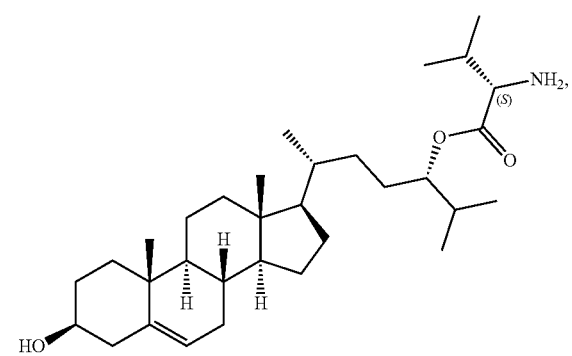

-continued
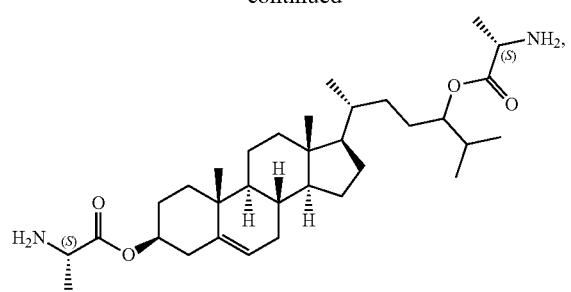
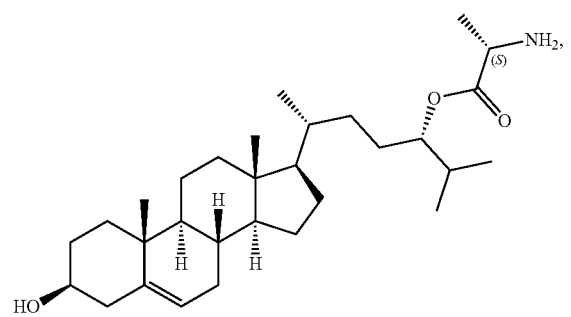
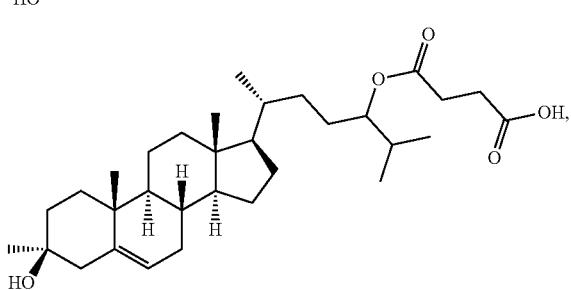
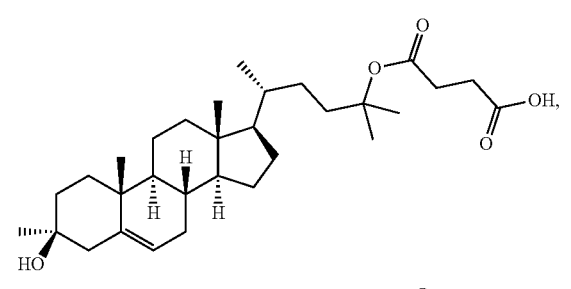
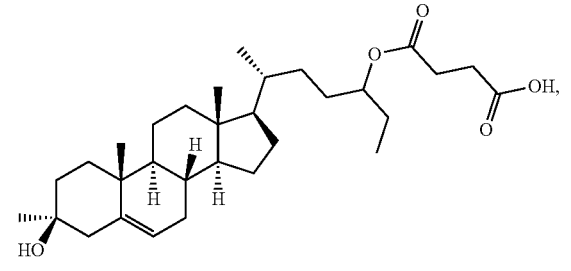
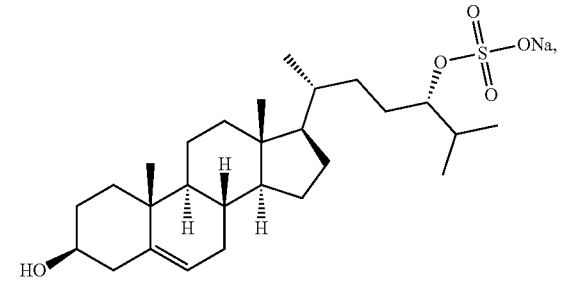
-continued
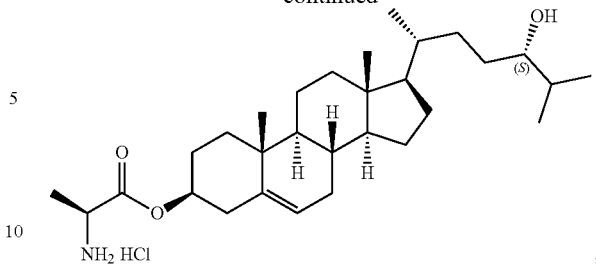
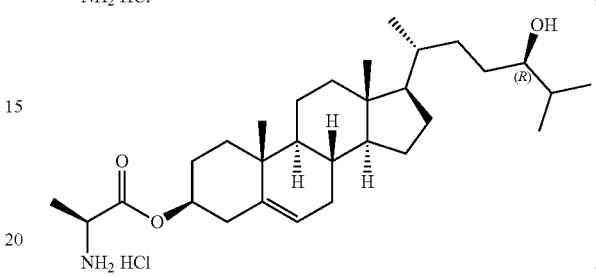
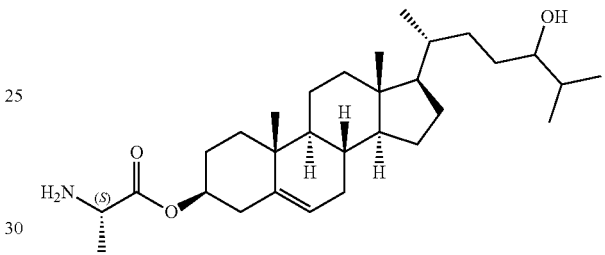
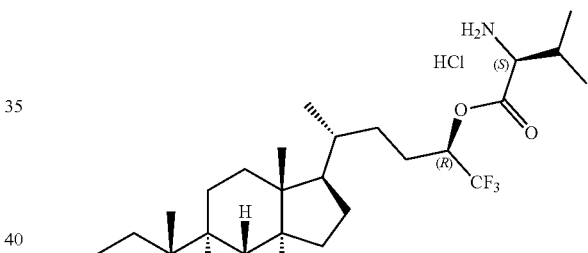
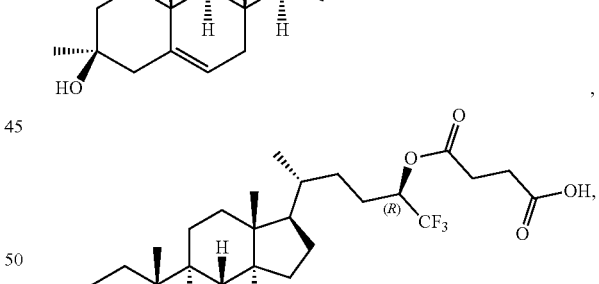
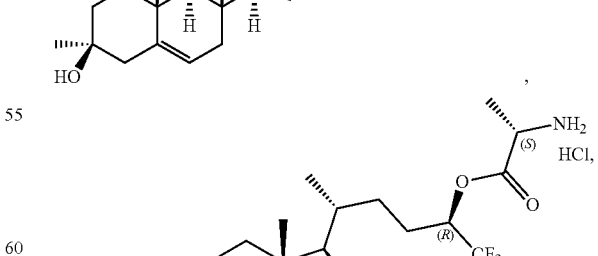
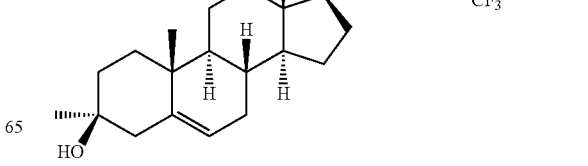

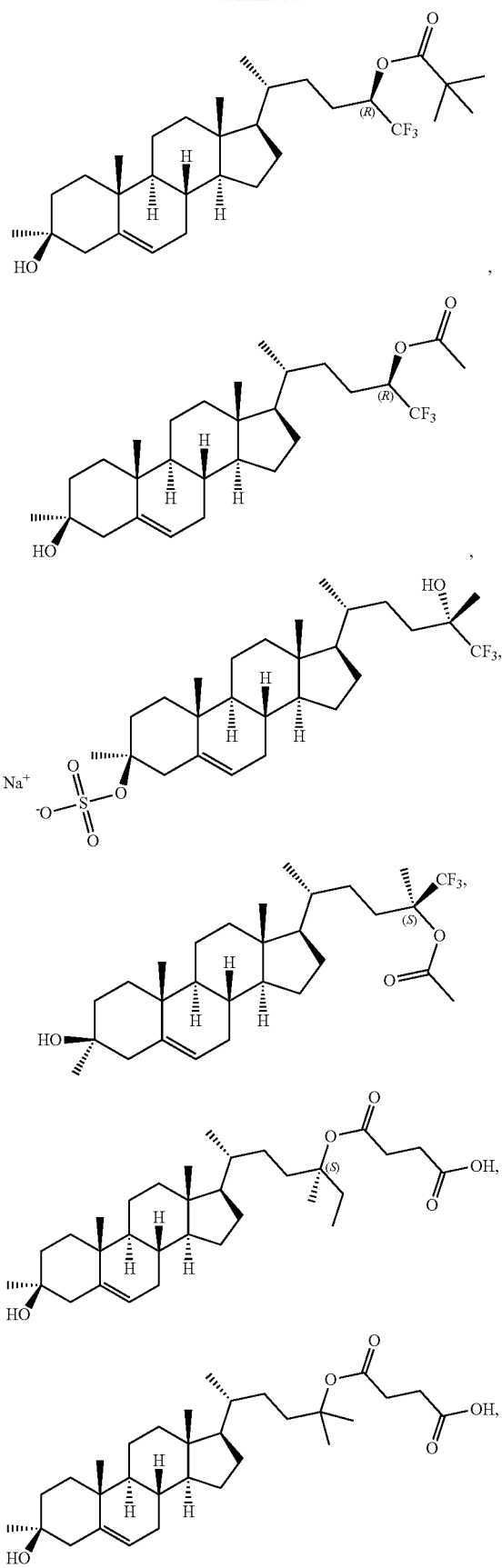
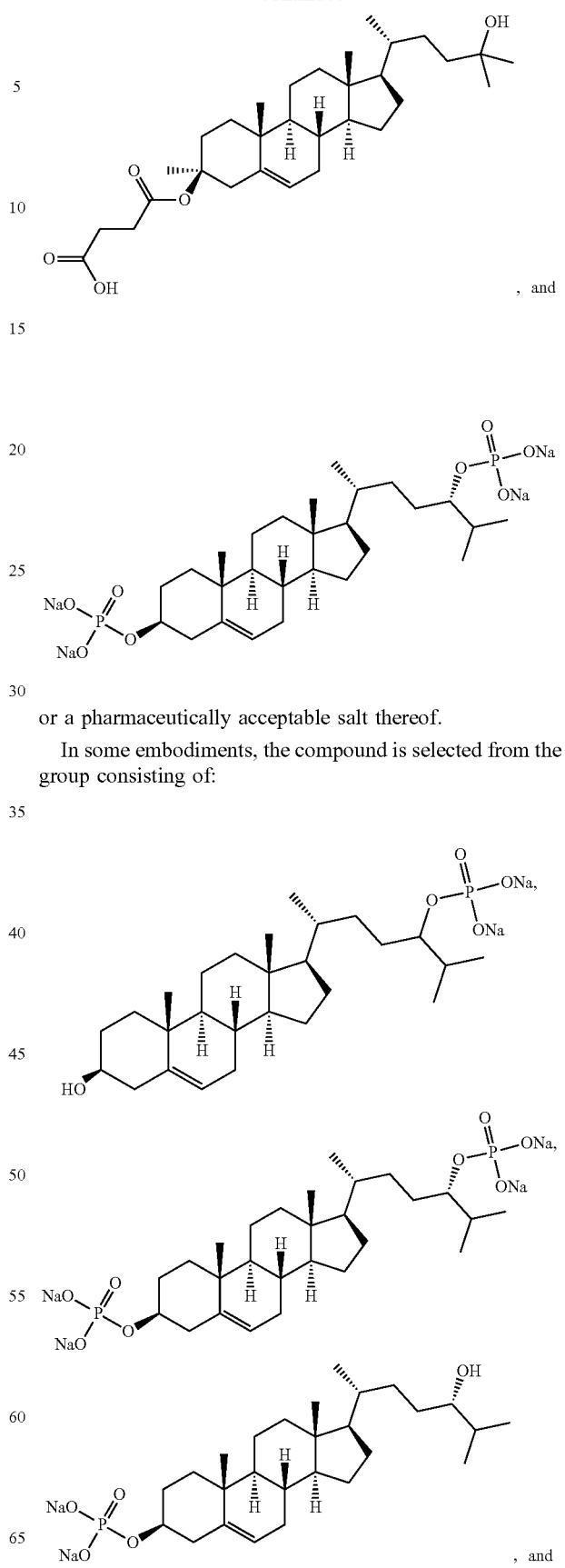
or a pharmaceutically acceptable salt thereof.
In some embodiments, the compound is selected from the group consisting of:

-continued

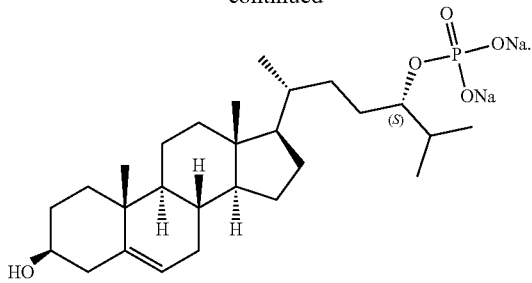

Pharmaceutical Compositions

In another aspect, the invention provides a pharmaceutical composition comprising a pharmaceutically acceptable carrier and a effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (I) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin. See, e.g., U.S. Pat. No. 5,376,645. In certain embodiments, the formulation comprises hexapropyl-β- cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules:

A compound of Formula (I), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid:

A compound of Formula (I), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection:

A compound of Formula (I), or pharmaceutically acceptable salt thereof, may be dissolved or suspended in a buffered sterile saline injectable aqueous medium to a concentration of approximately 5 mg/mL.

Exemplary Formulation 6—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets:

A compound of Formula (I), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets:

A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (I), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (I), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (I), or pharmaceutically acceptable salt thereof, may act as a negative allosteric modulator (NAM) of NMDA, and inhibit NMDA receptor function. In certain embodiments, the present invention, e.g., a compound of Formula (I), or pharmaceutically acceptable salt thereof, may act as positive allosteric modulators (PAM) of NMDA, and potentiate NMDA receptor function. In certain embodiments, the compound of Formula (I), or pharmaceutically acceptable salt thereof, modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Exemplary conditions related to NMDA-modulation includes, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, posttraumatic stress disorder, social phobia, generalized anxiety disorder), cognitive disorders (including Alzheimer's disease and other forms of dementia (e.g., frontotemporal dementia)), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain; headaches, e.g., migraine headaches), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (I), or pharmaceutically acceptable salt thereof, can be used to induce sedation or anesthesia. In certain embodiments, the compound of Formula (I), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, and tinnitus. In some embodiments, the disorder is Huntington's disease. In some embodiments, the disorder is Parkinson's disease. In some embodiments, the disorder is an inflammatory disease (e.g., lupus).

In another aspect, provided is a method of treating or preventing brain excitability in a subject susceptible to or afflicted with a condition associated with brain excitability, comprising administering to the subject an effective amount of a compound of the present invention, e.g., a compound of Formula (I), or a pharmaceutically acceptable salt thereof.

In yet another aspect, the present invention provides a combination of a compound of the present invention, e.g., a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Diseases and Disorders

Described herein are methods of treating a sterol synthesis disorder. Exemplary disorders are described herein. The methods include administering to a subject, e.g., a subject suffering from a sterol synthesis disorder such as SLOS, a NMDA receptor modulating compound. Exemplary compounds are described herein.

Sterol Synthesis Disorders

In one aspect, described herein are methods for treating a sterol synthesis disorder. Cholesterol has an essential rule in growth and development. It is a membrane lipid and a precursor to many molecules that play important roles in cellular growth and diffierentiation, protein glycosylation, and signaling pathways. Biosynthesis of cholesterol involves a number of enzymes and intermediates. Disorders resulting from a deficiency in any of the enzymes involved in cholesterol biosynthesis lead to the accumulation of intermediates and imbalance in biomolecules, resulting in disorders including congenital skeletal malformations, dysmorphic facial features, psychomotor retardation, and failure to thrive. In an embodiment, a sterol synthesis disorder or symptom of a sterol synthesis disorder can be treated by administering to a subject suffering from a sterol synthesis disorder a compound described herein, such as a NMDA receptor modulating compound as described herein. Additional disorders are described below.

Smith-Lemli-Opitz Syndrome

In one aspect, described herein are methods for treating Smith-Lemli-Opitz Syndrome (or SLOS, or 7-dehydrocholesterol reductase deficiency). SLOS is an inborn error of cholesterol synthesis. In addition to microcephaly, moderate to severe intellectual disability, sensory hypersensitivity, stereotyped behaviors, dysmorphic facial features, and syndactyly of the second/third toes, a feature of the disease is reduced cerebrosterol (24(S)-hydroxycholesterol) levels. SLOS is an autosomal recessive genetic condition resulting from deficiency in the final enzyme of the cholesterol synthesis pathway, and causes low or low-normal plasma cholesterol levels and increased 7- and 8-dehydrocholesterol (DHC; 7DHC and 8DHC) levels. Common therapies currently used include dietary cholesterol supplementation, treatment with 3-hydroxy-3-methylglutaryl coenzyme A reductase inhibitors (HMG CoA reductase inhibitors, also known as statins), and treatment with agents that enhance cholesterol production and/or accretion; and to decrease the accumulation of 7DHC and 8DHC, the potentially toxic precursors of cholesterol.

Desmosterolosis

Desmosterolosis is a deficiency in desmosterol reductase and has a similar phenotype to SLOS. In one aspect, described herein are methods for treating desmosterolosis with compounds described herein.

Sitosterolemia

Sitosterolemia is a rare autosomal recessive disorder caused by mutations in two ATP-binding cassette (ABC) transporter genes (ABCG5 and ABCG8). Sitosterolemia enhances the absorption of plant sterols and cholesterol from the intestines. Patients typically present with tendon and tuberous xanthomas and premature coronary artery disease. In one aspect, described herein are methods for treating sitosterolemia with compounds described herein.

Cerebrotendinous Xanthomatosis (CTX)

In one aspect, described herein are methods for treating cerebrotendinous xanthomatosis (also referred to as cerebral cholesterosis, or Van Bogaert-Scherer-Epstein syndrome) with compounds described herein. CTX can be caused by a mutation in the CYP27A1 gene, which produces the sterol 27-hydroxylase enzyme. Sterol 27-hydroxylase metabolizes cholesterol into bile acids (e.g., chenodeoxycholic acid) that are important in the absorption of fats in the intestine. Enzyme dysfunction can lead to cholesterol accumulation in tissues. CTX is characterized by childhood diarrhea, cataracts, tendon xanthomas, reduced mental capability and abnormal movements in adults.

Mevalonate Kinase Deficiency Syndromes (MKD)

Mevalonate Kinase Deficiency (also referred to as mevalonic aciduria (a more severe form of MKD), or Hyper IgD Syndrome (HIDS, or hyperimmunoglobulinemia D) with period fever syndrome (a more benign form of MKD)) causes an accumulation of mevalonic acid in the urine as a result of insufficient activity of mevalonate kinase. MKD can result in developmental delay, hypotonia, anemia, hepatosplenomegaly, dysmorphic features, mental retardation, and overall failure to thrive. Mevalonic aciduria is characterized by delayed physical and mental development, failure to thrive, recurrent episodes of fever with vomiting and diarrhea, enlarged liver, spleen and lymph nodes, microcephaly (small head size), cataract, low muscle tone, short statute, distinctfacial features, ataxia, and anemia. HIDS is characterized by recurrent episodes of fever associated with swollen lymph nodes, joint pain, gastrointestinal issues and skin rash. In one aspect, described herein are methods for treating MKD with the compounds described herein.

SC4MOL Gene Mutation (SMO Deficiency)

SC4MOL gene deficiency is a genetic disorder in the cholesterol biosynthesis pathway (e.g., mutations in the SC4MOL gene encoding a novel sterol oxidase). SC$MOL deficiency is characterized by the accumulation of dimethyl and monomethyl sterols that can be detected in blood, skin flakes or primary skin fibroblasts. In one aspect, described herein are methods for treating SMO deficiency with compounds described herein.

Niemann-Pick Disease

Niemann-Pick disease is a lysosomal storage disease resulting from a genetic mutation that affects metabolism. Niemann-Pick disease leads to abnormal accumulation of cholesterol and other fatty substances (lipids) due to an inability of the body to transport the substances. The accumulation damages the affected areas.

Autism

In one aspect, described herein are methods for treating autism spectrum disorder or autism. Autism spectrum disorder (ASD) and autism refer to a group of complex disorders of brain development. Autism is typically characterized by difficulties in social interaction, for example in verbal and nonverbal communication. Repetitive behaviors are also often seen in individuals having autism. Autism can be associated with intellectual disability, difficulties in motor coordination and attention and physical health issues, e.g., sleep and gastrointestinal disturbances. Individuals having autism can also excel in visual skills, music, math and art. Autism can refer to autistic disorder, childhood disintegrative disorder, pervasive developmental disorder—not otherwise specified (PDD-NOS), and Asperger syndrome. Autism also refers to monogenetic causes of autism such as synaptophathy's, e.g., Rett syndrome, Fragile X syndrome, Angelman syndrome.

Disorders Associated with Phenylketonuria

In one aspect, described herein are methods for treating disorders associated with phenylketonuria (e.g., cognitive disorders) with compounds described herein. Phenylketonuria can lead to hypochesterolemia and lowered vitamin D status. Total and low-density cholesterols and 25-hydroxy vitamin D have been found to be decreased in subjects suffering from phenylketonuria as compared with subjects not suffering from phenylketonuria (*Clin. Chim. Acta* 2013, 416: 54-59). 24S-hydroxycholesterol and 27S-hydroxycholesterol and 7α-hydroxycholesterol (e.g., representing peripheral and hepatic cholesterol elimination, respectively) have been shown to be significantly decreased in subjects suffering from phenylketonuria, while 7β-hydroxycholesterol (e.g., reflecting oxidative stress) was increased significantly in subjects suffering from phenylketonuria. Changes in the levels of 24S—OHC and 7β-hydroxycholesterol correlate with phenylalanine level, and 27S-hydroxycholesterol levels may correlate with the 25-hydroxy vitamin D level in subjects suffering from phenylketonuria.

Abbreviation:

DCC: dicyclohexylcarbodiimide; DMAP: 4-dimethylaminopyridine; TEA: triethylamine; AlaOH: alanine; Boc: t-butoxycarbonyl. Py: pydidine; THF: tetrahydrofuran; TMS: trimethylsilyl; TBS (TBDMS): t-butyldimethylsilyl; Na$_2$SO$_4$: sodium sulfate; PE: petroleum ether; DCM: dichloromethane; EtOAc: ethylacetate, MeOH: methanol; Py: pyridine, Boc: t-butoxycarbonyl; MTBE: methyl tert-butyl ether.

EXAMPLES

In order that the invention described herein may be more fully understood, the following examples are set forth. Synthetic methods or intermediates may be found, for example in WO2014/160480*. The synthetic and biological examples described in this application are offered to illustrate the compounds, pharmaceutical compositions, and methods provided herein and are not to be construed in any way as limiting their scope.

The stereochemistry assigned herein (e.g., the assignment of "R" or "S" to the C24 position of the steroid) may be tentatively (e.g., randomly) assigned. For example, a C24 position may be drawn in the "R" configuration when the absolute configuration is "S." A C24 position may also be drawn in the "S" configuration when the absolute configuration is "R."

Example 1. Synthesis of Compound 1

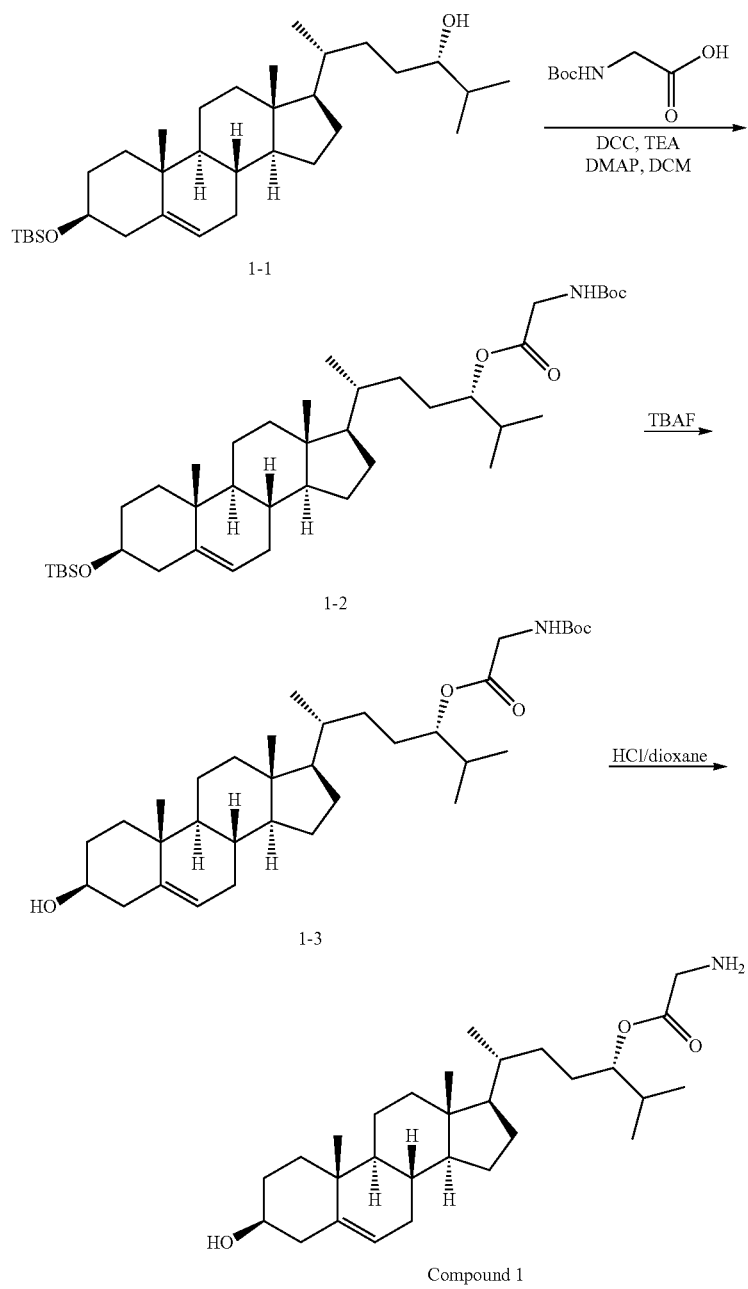

Compound 1

Synthesis of Compound 1-2

To a solution of Compound 1-1 (0.3 g, 0.58 mmol; synthesized as described in Takahashi et al., Tetrahedron Letters, 2003, 44(2), 341-344) in DCM (10 mL) was added DMAP (7.08 mg, 0.058 mmol), TEA (95.7 mg, 0.87 mmol), DCC (179 mg, 0.87 mmol) and 2-((tert-butoxycarbonyl)amino)acetic acid (203 mg, 1.16 mmol). The mixture was stirred at 15° C. for 16 hours, at which point an additional aliquot of DMAP (7.08 mg, 0.058 mmol), TEA (95.7 mg, 0.87 mmol), DCC (179 mg, 0.87 mmol) and 2-((tert-butoxycarbonyl)amino)acetic acid (203 mg, 1.16 mmol) were added. The mixture was stirred at 25° C. for 16 hours, then the mixture was filtered and the filtrate was diluted with aqueous sat. $NH_4Cl$ (30 mL) and extracted with DCM (10 mL×2). The combined organic phases were dried over $Na_2SO_4$, filtered, and concentrated to give the crude product Compound 1-2, which was used in the next step directly without purification. $^1H$ NMR indicated an estimated yield of 45%.

Synthesis of Compound 1-3

Compound 1-2 (350 mg, 0.519 mmol) was dissolved in TBAF (5.18 mL, 5.18 mmol, 1M in THF) and the mixture was stirred at 15° C. for 16 hours. The mixture was quenched with saturated NH₄Cl (10 mL) and extracted with EtOAc (5 mL×2). The combined organic phase was dried over Na₂SO₄, filtered, concentrated, and purified by silica gel (PE:EtOAc=10:1) to give the crude product Compound 1-3 (250 mg, Compound 1-2/Compound 1-3=0.55/0.45) product as a colorless oil.

Synthesis of Compound 1

Compound 1-3 was dissolved in HCl/dioxane (4 N, 5 mL), and the mixture was stirred at 15° C. for 30 minutes. Then MTBE (5 mL) was then added to the mixture to form a precipitate, which was filtered and purified by prep-HPLC (column: Phenomenex Synergi C18 150*30 mm*4 um, gradient: 36-66% B (A=0.05% HCl-ACN, B=acetonitrile) flow rate: 30 mL/min) to afford the HCl salt of Compound 1 (6 mg, 2.92%) as an off white solid. ¹H NMR (400 MHz, MeOD) δ 5.36-5.35 (m, 1H), 3.91-3.81 (m, 2H), 3.43-3.38 (m, 1H), 2.68-2.25 (m, 2H), 2.10-0.94 (m, 37H), 0.74 (s, 3H). LCMS MS ESI calcd. for $C_{29}H_{49}NO_3Na$ [M+Na]⁺482, found 482.

Example 2. Synthesis of Compound 2

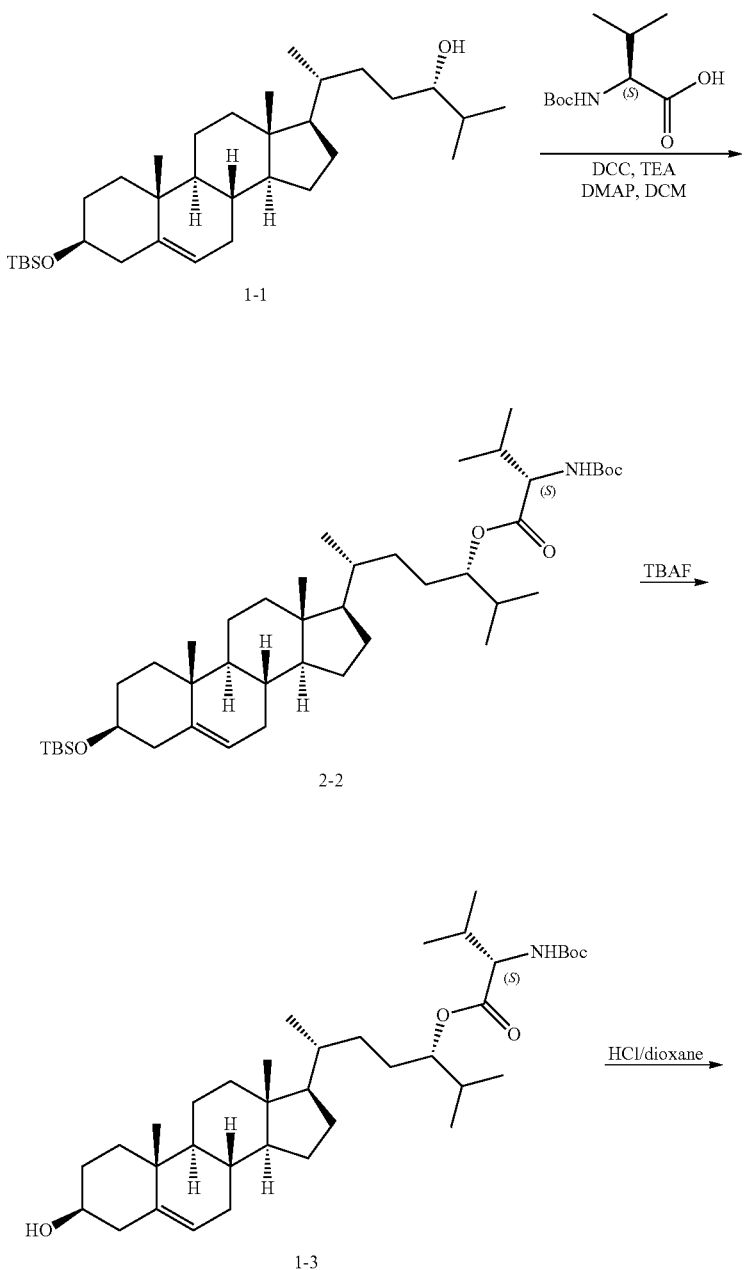

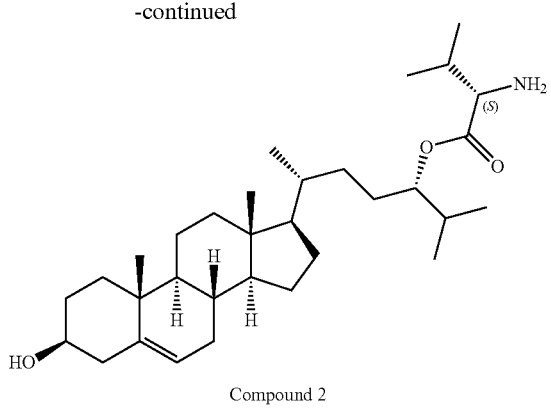

Compound 2

Synthesis of Compound 2-2

To a solution of Compound 1-1 (0.3 g, 0.58 mmol) in DCM (10 mL) was added DMAP (21.2 mg, 0.174 mmol), TEA (191 mg, 1.74 mmol), DCC (452 mg, 1.74 mmol) and (S)-2-((tert-butoxycarbonyl)amino)-3-methylbutanoic acid (378 mg, 1.74 mmol). The mixture was stirred at 25° C. for 16 hours. The mixture was filtered, the filtrate was concentrated and purified by combi-flash (PE: EA=100%-95%) to give Compound 2-2 (380 mg, 92%) as a colorless oil. $^1$H NMR (400 MHz, CDCl$_3$) δ 5.31-5.19 (m, 1H), 5.03-4.99 (m, 1H), 4.74-4.72 (m, 1H), 4.23-4.20 (m, 1H), 3.50-3.44 (m, 1H), 2.29-2.17 (m, 3H), 1.85-0.85 (m, 60H), 0.66 (s, 3H), 0.05 (s, 6H).

Synthesis of Compound 2-3

Compound 2-2 (380 mg, 0.53 mmol) in TBAF (15.9 mL, 15.9 mmol, 1M in THF) was stirred at 15° C. for 16 hours. The mixture was quenched with aqueous sat. NH$_4$Cl (20 mL) and extracted with EtOAc (10 mL×2). The combined organic phase was dried over Na$_2$SO$_4$, filtered, concentrated, and purified by combi-flash (PE: EA=100%-90%) to give Compound 2-3 as a colorless oil. $^1$H NMR (400 MHz, CDCl$_3$) δ 5.35-5.29 (m, 1H), 5.01-4.99 (m, 1H), 4.75-4.73 (m 1H), 4.23-4.20 (m, 1H), 3.52-3.50 (m, 1H), 2.29-2.17 (m, 3H), 1.85-0.85 (m, 52H), 0.66 (s, 3H).

Synthesis of Compound 2

Compound 2-3 (50 mg, 0.083 mmol) was dissolved in HCl/dioxane (1 mL) and stirred at 15° C. for 30 minutes. Then MTBE (1 mL) was then added to the mixture and a precipitate was formed, which was filtered to afford the HCl salt of Compound 2 (5 mg, 12.0%) as an off-white solid. $^1$H NMR (400 MHz, MeOD) δ 5.36-5.30 (m, 1H), 3.97-3.80 (m, 1H), 3.50-3.40 (m, 1H), 2.50-2.40 (m, 3H), 2.35-0.85 (m, 46H), 0.74 (s, 3H). LCMS MS ESI calcd. for $C_{32}H_{56}NO_3$ [M+H]$^+$ 502, found 502.

Example 3. Synthesis of Compound 3

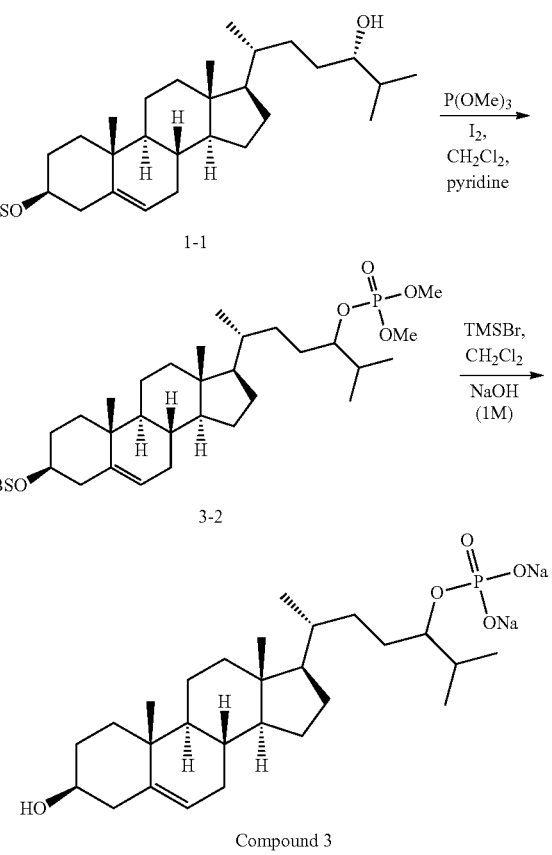

Synthesis of 3-2

Iodine (1.17 g, 4.63 mmol) was added to a solution of trimethyl phosphite (526 mg, 4.24 mmol) in CH$_2$Cl$_2$ (20 mL) at 0° C. After stirring for 5 minutes, the clear colorless solution was allowed to warm to 15° C. The phosphorylating agent was added dropwise to a solution of Compound 1-1 (2.0 g, 3.86 mmol) and pyridine (1.21 g, 15.4 mmol) in CH$_2$Cl$_2$ (30 mL) at 0° C. The resulting mixture was stirred at 0° C. for 1 h, then cooled to 15° C. and stirred for another 1 h. The reaction mixture was treated water (50 mL), extracted with CH$_2$Cl$_2$ (50 mL×2). The combined organic phase was washed with brine (50 mL), dried over anhydrous Na$_2$SO$_4$, filtered, and concentrated under vacuum. The residue was purified by column chromatography on silica gel (PE/EtOAc=10/1 to 3/1) to afford Compound 3-2 (1.8 g, 75%) as an off-white solid. $^1$H NMR (400 MHz, CDCl$_3$) δ 5.35-5.30 (m, 1H), 4.20-4.17 (m, 1H), 3.76 (s, 3H), 3.73 (s, 3H), 3.48-3.46 (m, 1H), 2.26-2.15 (m, 2H), 1.93-1.61 (m, 7H), 1.55-0.88 (m, 38H), 0.66 (s, 3H), 0.05 (s, 6H).

Synthesis of Compound 3

To a solution of Compound 3-2 (300 mg, 480 μmol) in CH$_2$Cl$_2$ (5 mL) was added bromotrimethylsilane (220 mg, 1.44 mmol) at 15° C. and the reactions was stirred for 12 h. The reaction mixture was adjusted to pH=8 with aq. NaOH (1.44 mL, 1.44 mmol, 1 M in H$_2$O) and a precipitate was formed, which was then filtered, washed with CH$_2$Cl$_2$ (2 mL) and water (2 mL), and dried under vacuum to afford Compound 3 (30 mg, 12%) as an off-white solid. $^1$H NMR (400 MHz, DMSO-d$_6$) δ 5.24-5.23 (m, 1H), 3.87-3.85 (m, 1H), 3.24-3.21 (m, 1H), 2.13-2.06 (m, 2H), 1.91-1.60 (m, 6H), 1.50-0.80 (m, 33H), 0.62 (s, 3H). LCMS MS ESI calcd. for C$_{27}$H$_{44}$ [M+H−H$_2$O—Na$_2$O$_4$P]$^+$367, found 367. HRMS MS ESI calcd. for C$_{27}$H$_{46}$O$_5$P [M−H]$^-$ 481.3088, found 481.3105.

Example 4. Synthesis of Compound 4

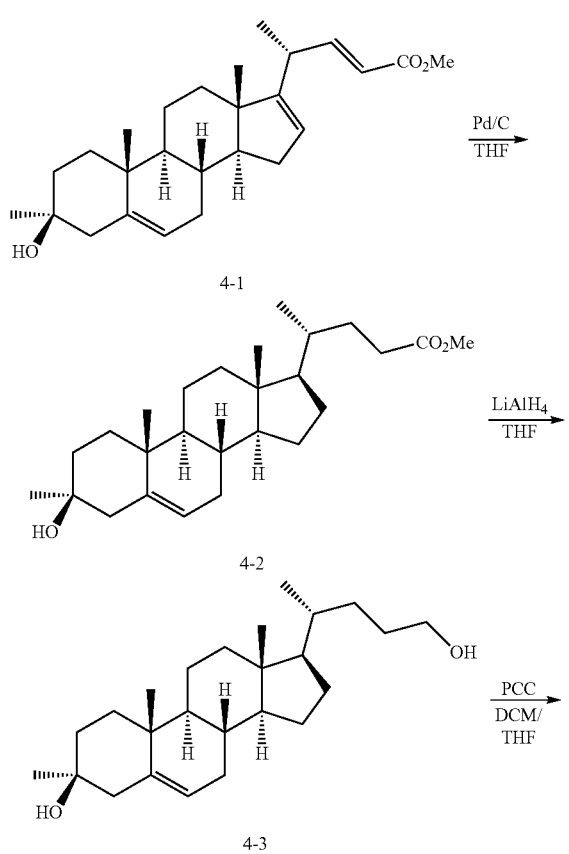

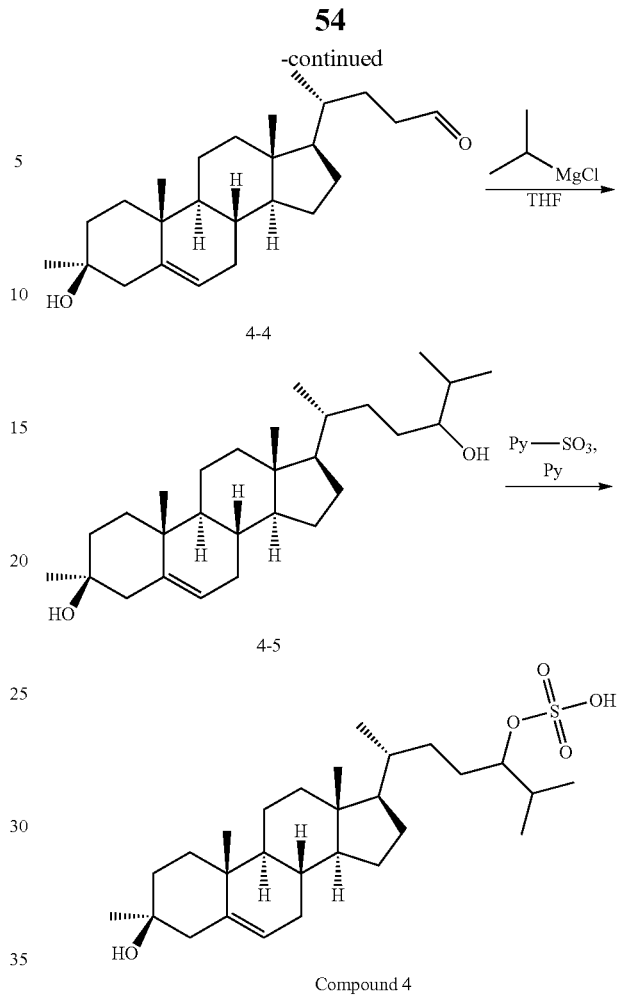

Compound 4

Synthesis of Compound 4-2

To a solution of Compound 4-1* (2 g, 5.01 mmol) and Pd/C (200 mg, 10%) in THF (30 mL) was hydrogenated under 15 psi of hydrogen at 25° C. for 3 h. The mixture was filtered through a pad of celite and the filtrate was concentrated in vacuum to afford Compound 4-2 (1.8 g, crude) as an off-white solid.

Synthesis of Compound 4-3

To a solution of Compound 4-2 (1.8 g, 4.47 mmol) in THF (25 mL) was added a solution LiAlH$_4$ (339 mg, 8.94 mmol) in THF (5 mL) drop wise below 15° C. The solution was stirred at 15° C. for 2 h. The reaction was quenched by the addition of saturated aqueous NH$_4$Cl (20 mL) at 0° C. The resulting mixture was extracted with EtOAc (2×50 mL). The combined organic layer was washed with brine (2×30 mL) and concentrated in vacuum to afford Compound 4-3 (1.6 g, crude) as a light yellow solid.

Synthesis of Compound 4-4

A mixture of Compound 4-3 (1.6 g, 4.27 mmol) in DCM (10 mL) and THF (10 mL) was added PCC (2.27 g, 10.6 mmol) at 25° C. The reaction was stirred at 25° C. for 3 hrs. The solution was filtered and the filter cake was washed with DCM (25 mL). The combined filtrate was concentrated in vacuum. The residue was purified by silica gel column, eluting with PE/EtOAc=8/1 to give Compound 4-4 (0.9 g, 54%) as an off-white solid.

Synthesis of Compound 4-5

To a solution of Compound 4-4 (0.9 g, 2.41 mmol) in THF (30 mL) was added drop wise isopropyl magnesium chloride (3.61 mL, 7.23 mmol, 2M in THF) at −78° C. The mixture was stirred at −78° C. for 2 hrs. Then, the mixture was allowed to warm up to 25° C. and stirred for 3 hrs. The reaction was poured into water (100 mL) and extracted with EtOAc (2×30 mL). The combined organic layer was washed with brine (50 mL), dried over $Na_2SO_4$ and concentrated in vacuum. The residue was purified by silica gel column, eluting with PE/EtOAc=5/1 to afford Compound 4-5 (0.6 g, 57%) as an off-white solid.

Synthesis of Compound 4

To a solution of Compound 4-5 (200 mg, 479 μmol) in pyridine (3 mL) was added $SO_3$—Py (76.1 mg, 4.79 mmol), and the mixture was stirred at 40° C. for 16 hours. Pyridine was removed under reduced pressure and the residue was diluted with NaOH (3% in water, 20 mL), then extracted with BuOH (10 mL×3). The combined organic phase was dried over $Na_2SO_4$, filtered, concentrated, and purified by combi-flash (DCMin MeOH=100%-75%) to give Compound 4 (6 mg, 2%) as an off-white solid. $^1H$ NMR (400 MHz, DMSO-$d_6$) δ 5.25-5.19 (m, 1H), 4.35 (brs, 1H), 3.85-3.75 (m, 1H), 1.95-0.79 (m, 41H), 0.65 (m, 3H). LCMS MS ESI calcd. for $C_{28}H_{47}O_4S$ $[M+H-H_2O]^+$479, found 479.

Example 5. Synthesis of Compound 5

Synthesis of Compound 5-2A and Compound 5-2B

Molecular iodine (1.10 g, 4.34 mmol) was added to a solution of trimethyl phosphite (584 mg, 4.71 mmol) in $CH_2Cl_2$ (3 mL) at 0° C. After stirring for 5 minutes, the clear, colorless solution was warmed to 20° C. and added dropwise to a solution of Compound 5-1 (500 mg, 1.24 mmol) and pyridine (783 mg, 9.92 mmol) in $CH_2Cl_2$ (2 mL) at 0° C. The resulting mixture was stirred at 0° C. for 1 h, then warmed to 20° C. and stirred for another 1 h. The reaction mixture was treated with water (20 mL) and extracted with $CH_2Cl_2$ (20 mL×2). The combined organic phase was washed with brine (20 mL), dried over anhydrous $Na_2SO_4$, filtered, concentrated under vacuum, and purified on silica gel (PE/EtOAc=8/1 to 3/1) to afford Compound 5-2A (200 mg, 32%) as an off-white solid and Compound 5-2B (50 mg, 7%) as a light yellow oil. Compound 5-2A: $^1H$ NMR (400 MHz, $CDCl_3$) δ 5.39-5.35 (m, 1H), 4.30-4.18 (m, 2H), 3.77 (s, 6H), 3.74 (s, 6H), 2.44-2.40 (m, 2H), 1.98-1.57 (m, 8H), 1.48-0.92 (m, 28H), 0.67 (s, 3H). Compound 5-2B: $^1H$ NMR (400 MHz, $CDCl_3$) δ 5.39-5.36 (m, 1H), 4.25-4.18 (m, 1H), 3.77 (s, 3H), 3.74 (s, 3H), 3.35-3.25 (m, 1H), 2.44-2.40 (m, 2H), 1.99-1.57 (m, 8H), 1.57-0.88 (m, 29H), 0.68 (s, 3H).

Synthesis of Compound 5

To a solution of Compound 5-2A (50 mg, 80.8 μmol μmol) in $CH_2Cl_2$ (3 mL) was added TMSBr (74.1 mg, 484.8 μmol μmol) at 20° C. and the mixture stirred for 12 hrs, at which point TLC analysis indicated the starting material was consumed completely. The reaction mixture was adjusted to

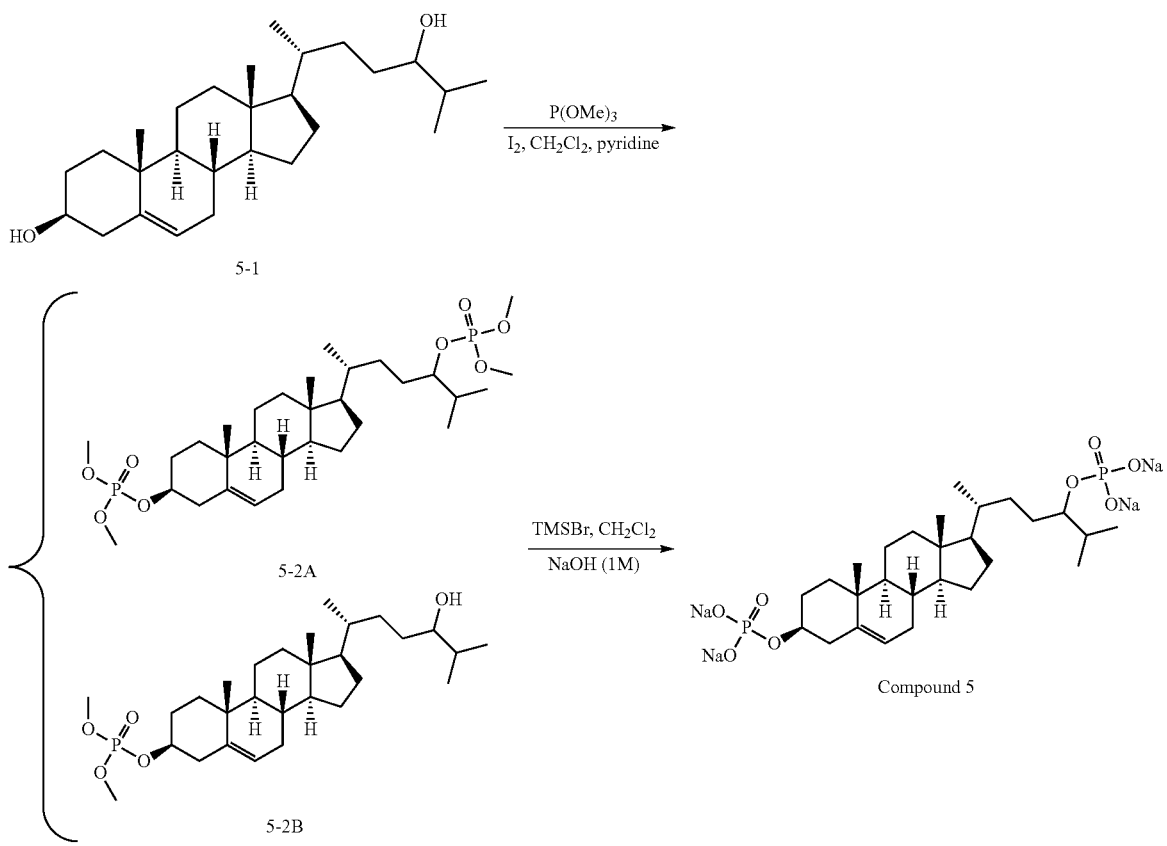

pH=8 with aq. NaOH (484 uL, 484 µmol, 1 M in H₂O) and a precipitate was formed. The white solid was filtered and washed with CH₂Cl₂ (2 mL) and water (2 mL), and dried under vacuum to afford Compound 5 (9.8 mg, 19%) as an off-white solid. ¹H NMR (400 MHz, DMSO-d₆) δ 5.30-5.25 (m, 1H), 3.95-3.80 (m, 2H), 2.37-2.26 (m, 1H), 2.26-2.15 (m, 1H), 1.96-1.77 (m, 6H), 1.55-0.79 (m, 30H), 0.62 (s, 3H). LCMS MS ESI calcd. for $C_{27}H_{43}$ [M+H–2H₃PO₄]⁺ 367, found 367. HRMS MS ESI calcd. for $C_{27}H_{47}O_8P_2$ [M–H]⁻ 561.2752, found 561.2760.

Example 6. Synthesis of Compound 6

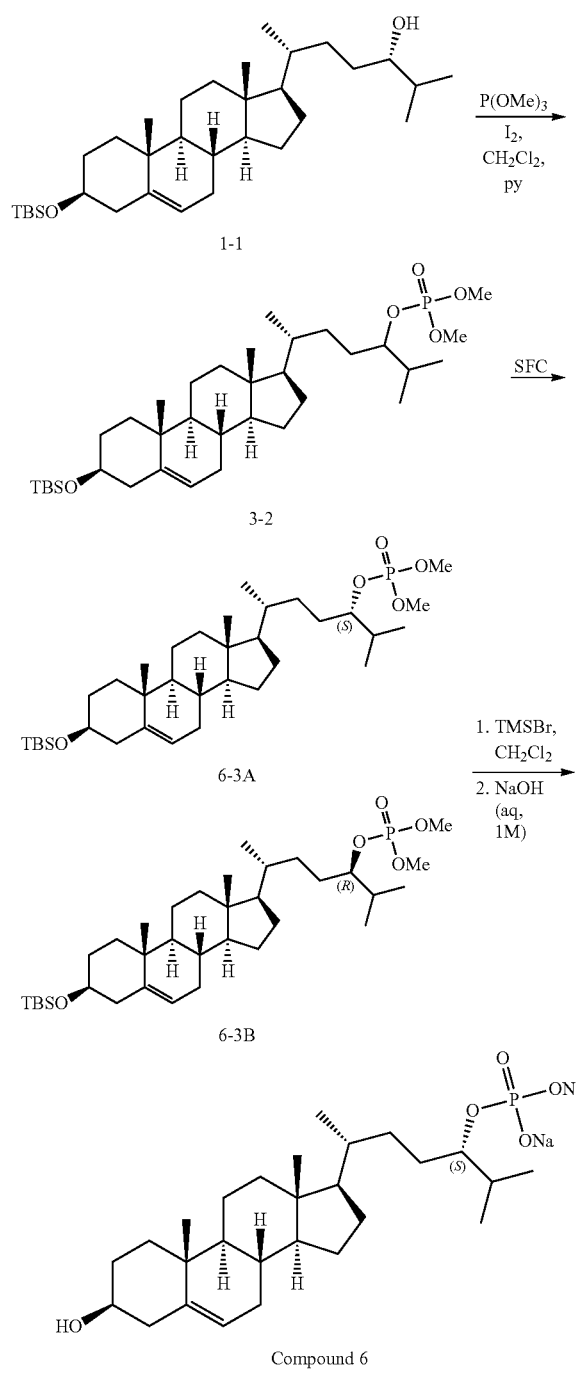

Synthesis of Compound 3-2

Iodine (1.17 g, 4.63 mmol) was added to a solution of trimethyl phosphite (526 mg, 4.24 mmol) in CH₂Cl₂ (20 mL) at 0° C. After stirring for 5 minutes, the clear, colorless solution was allowed to warm to 15° C., after which it was added dropwise to a solution of Compound 1-1 (1.21 g, 15.4 mmol) in CH₂Cl₂ (30 mL) at 0° C. The resulting mixture was stirred at 0° C. for 1 h and then warmed to 15° C. and stirred for another 1 h. The reaction mixture was treated water (50 mL), extracted with CH₂Cl₂ (50 mL×2), and the combined organic phase was washed with brine (50 mL), dried over anhydrous Na₂SO₄, filtered, and concentrated under vacuum. The residue was purified on silica gel (PE/EtOAc=10/1 to 3/1) to afford Compound 3-2 (1.8 g, 75%) as an off-white solid. ¹H NMR (400 MHz, CDCl₃) δ 5.35-5.30 (m, 1H), 4.20-4.18 (m, 1H), 3.76 (s, 3H), 3.73 (s, 3H), 3.48-3.46 (m, 1H), 2.26-2.17 (m, 2H), 1.95-1.61 (m, 7H), 1.48-0.88 (m, 41H), 0.66 (s, 3H), 0.05 (s, 6H).

Synthesis of Compound 6-3A and Compound 6-3B

Compound 3-2 (1.5 g, 2.40 mmol) was dissolved in MeOH (20 mL) and separated by supercritical fluid chromatography (SFC) to afford Compound 6-3A (490 mg, 33%) and Compound 6-3B (400 mg, 27%) as off-white solids. ¹H NMR (400 MHz, CDCl₃) δ 5.30-5.25 (m, 1H), 4.20-4.18 (m, 1H), 3.76 (s, 3H), 3.73 (s, 3H), 3.48-3.44 (m, 1H), 2.30-2.10 (m, 2H), 1.98-1.57 (m, 7H), 1.53-0.88 (m, 38H), 0.67 (s, 3H), 0.05 (s, 6H). ¹H NMR (400 MHz, CDCl₃) δ 5.30-5.25 (m, 1H), 4.20-4.17 (m, 1H), 3.76 (s, 3H), 3.73 (s, 3H), 3.50-3.44 (m, 1H), 2.26-2.10 (m, 2H), 1.98-1.62 (m, 11H), 1.48-0.88 (m, 34H), 0.67 (s, 3H), 0.05 (s, 6H). For 6-3B, 91% de was obtained that was not subjected to deprotection.

Synthesis of 6

To a solution of Compound 6-3A (100 mg, 160 µmol) in CH₂Cl₂ (3 mL) was added TMSBr (97.9 mg, 640 µmol) and the reaction was stirred f at 20° C. or 12 h. The reaction mixture was adjusted to pH=8 with aq. NaOH (640 uL, 640 µmol, 1 M in H₂O) and the solid was precipitated. The white solid was filtered and washed with CH₂Cl₂ (2 mL), water (2 mL), dried by vacuum to provide Compound 6 (45.7 mg, 54%) as an off-white solid. ¹H NMR (400 MHz, DMSO-d₆) δ 5.30-5.20 (m, 1H), 3.89-3.80 (m, 1H), 3.26-3.20 (m, 1H), 2.15-1.60 (m, 8H), 1.55-0.80 (m, 30H), 0.63 (s, 3H). LCMS Rt=1.330 min in 2.0 min chromatography, 10-80 AB, MS ESI calcd. for $C_{27}H_{43}$ [M+H–H₃PO₄–H₂O]⁺367, found 367. HRMS MS ESI calcd. for $C_{27}H_{46}O_5P$ [M–H]⁻ 481.3088, found 481.3085.

Example 7. Synthesis of Compound 7

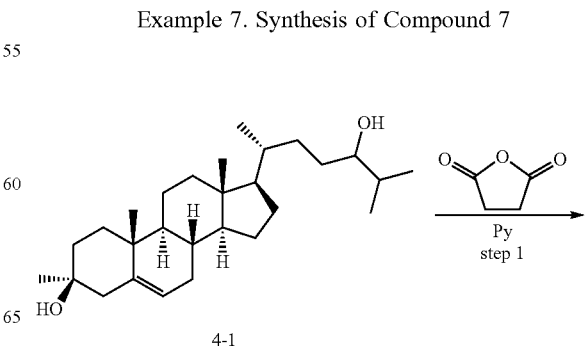

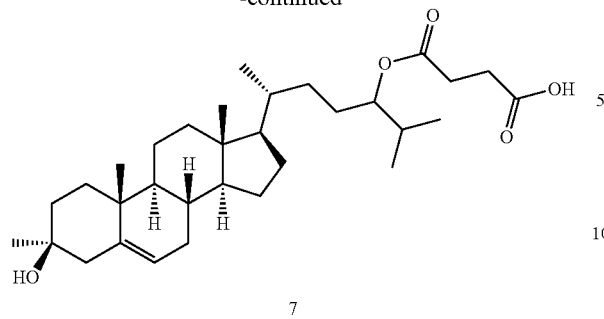

7

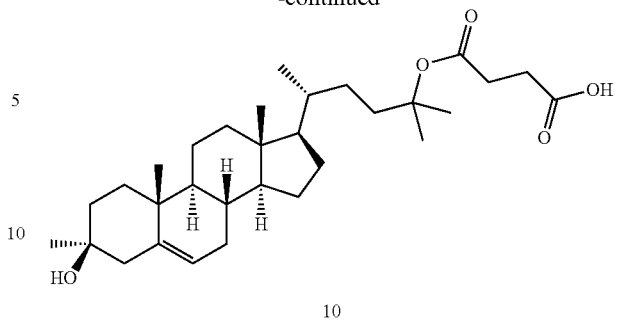

10

To a solution of Compound 4-1 (0.1 g, 0.239 mmol) in pyridine (2 mL) was added dihydrofuran-2,5-dione (71.7 mg, 0.717 mmol) and DMAP (14.5 mg, 0.119 mmol). The mixture was stirred at 15° C. for 16 hours. To the reaction was added aqueous sat. NH$_4$Cl (10 mL) and extracted with EtOAc (2×5 mL). The combined organic phase was dried over Na$_2$SO$_4$, filtered, concentrated and purified by combi-flash (PE: EA=100%-70%, DCM: MeOH=100%-95%) to give Compound 7 (40 mg) as colorless oil, which was washed with PE (5 mL) and filtered to give Compound 7 (10 mg, yield 8%) as an off-white solid. $^1$H NMR (400 MHz, CDCl$_3$) δ 5.30-5.29 (m, 1H), 4.73-7.70 (m, 1H), 2.67-2.63 (m, 4H), 2.45-2.35 (m, 1H), 1.99-1.95 (m, 3H), 1.85-0.80 (m, 39H), 0.66 (s, 3H). LCMS t$_R$=1.591 min in 2 min chromatography, 10-80AB_ELSD, MS ESI calcd. for C$_{32}$H$_{52}$O$_5$Na [M+Na]$^+$ 539, found 539.

Example 10. Synthesis of Compound 10

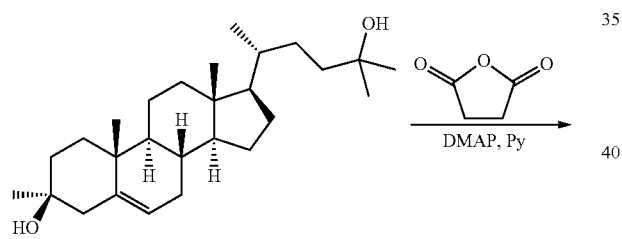

10-1

To a solution of Compound 10-1 (50 mg, 0.124 mmol; synthesized as described in Upasani et al., WO2013/36835, [00375]) in pyridine (2 mL) was added dihydrofuran-2,5-dione (37.2 mg, 0.372 mmol) and DMAP (7.57 mg, 0.062 mmol). The mixture was stirred at 15° C. for 16 hours and then another batch of dihydrofuran-2,5-dione (37.2 mg, 0.372 mmol) and DMAP (7.57 mg, 0.062 mmol) was added. The mixture was stirred at 15° C. for 16 hours. The reaction solution was quenched with aqueous sat. NH$_4$Cl (5 mL) and extracted with EtOAc (3 mL×2). The combined organic phase was dried over Na$_2$SO$_4$, filtered, concentrated. The residue was purified by combi-flash (0-30% of EtOAc in PE) to give 50 mg of impure Compound 10. The mixture was further purified by prep-HPLC (column: Gemini 150*25 5u, gradient: 65-65% B (A=0.05% HCl-ACN, B=acetonitrile) to give Compound 10 (5 mg, 8% yield) as an off-white solid. $^1$H NMR (400 MHz, CDCl3) δ 5.35-5.25 (m, 1H), 2.60-2.55 (m, 5H), 2.45-2.35 (m, 2H), 2.10-0.80 (m, 39H), 0.67 (s, 3H). LCMS t$_R$=1.523 min in 2 min chromatography, 10-80AB_ELSD, MS ESI calcd. for C$_{31}$H$_{50}$O$_5$Na [M+Na]$^+$ 525, found 525.

Example 11. Synthesis of Compound 11

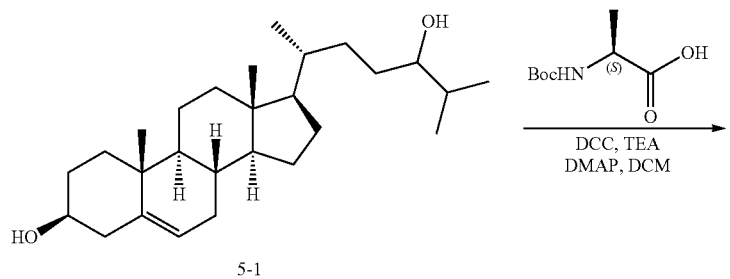

5-1

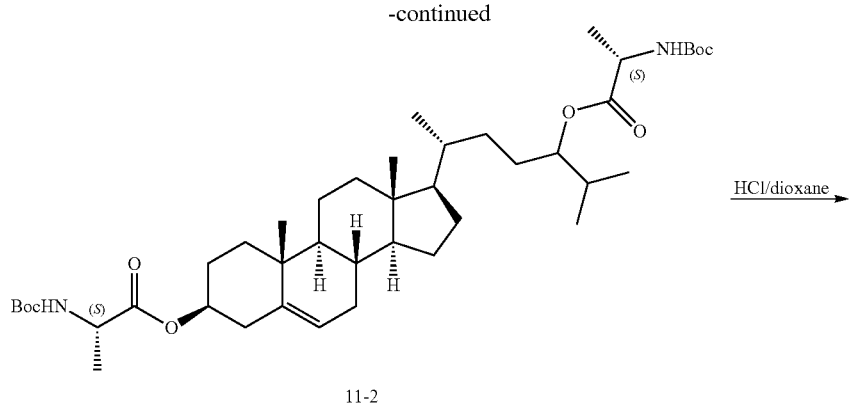

11-2

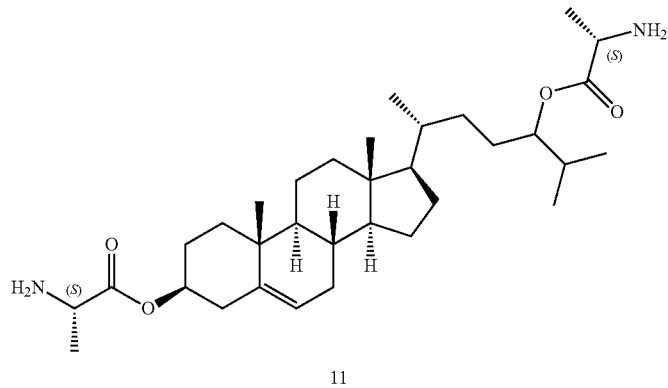

11

Synthesis of Compound 11-2

To a solution of Compound 5-1 (300 mg, 745 μmol) and (S)-2-((tert-butoxycarbonyl)amino)propanoic acid (423 mg, 2.41 mmol) in DCM (5 mL) was added DCC (767 mg, 3.72 mmol), DMAP (45 mg, 368 μmol), TEA (452 mg, 4.47 mmol). The mixture was stirred at 30° C. for 3 hours. The mixture was washed by brine (10 mL) and extracted by EtOAc (20 mL×2). The combined organic layer was dried by $Na_2SO_4$, filtered and evaporated in vacuum. The residue was purified by silica gel chromatography (PE/EtOAc=5/1) to afford Compound 11-2 (300 mg, 54% yield) as a yellow oil. $^1H$ NMR (400 MHz, $CDCl_3$) δ 5.40-5.37 (m, 1H), 5.17-5.04 (m, 2H), 4.76-4.61 (m, 2H), 4.30-4.17 (m, 2H), 2.36-2.30 (m, 2H), 2.00-1.95 (m, 2H), 1.88-1.77 (m, 4H), 1.61-0.88 (m, 54H), 0.67 (s, 3H).

Synthesis of Compound 11

Compound 11-2 (150 mg, 209 μmol) was added to HCl/dioxane (3 mL, 4M). The mixture was stirred at 25-27° C. for 1 hour. The mixture was filtered and washed with MTBE (5 mL×2), dried in vacuum to give an off-white solid. The solid was dissolved in water/MeCN (5 mL/1 mL) and lyophilized 3 times to remove residual solvent to afford Compound 11 (71 mg, yield 43% yield) as an off-white solid. $^1H$ NMR (400 MHz, MeOD) δ5.45-5.44 (m, 1H), 4.74-4.66 (m, 1H), 4.17-4.05 (m, 2H), 2.44-2.37 (m, 2H), 2.09-1.87 (m, 6H), 1.72-0.95 (m, 37H), 0.75 (s, 3H). LCMS Rt=0.831 min in 2.0 min chromatography, 30-90 AB, MS ESI calcd. for $C_{33}H_{57}N_2O_4$ $[M+H]^+$ 545, found 545.5.

Example 12. Synthesis of Compound 12

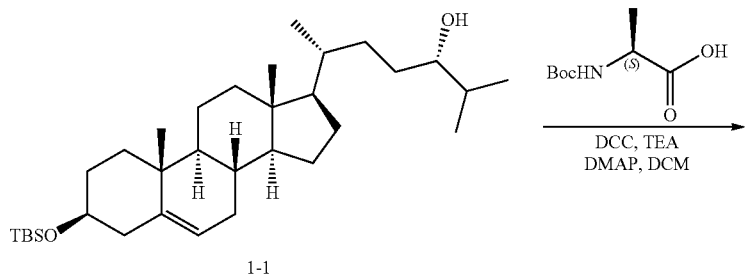

1-1

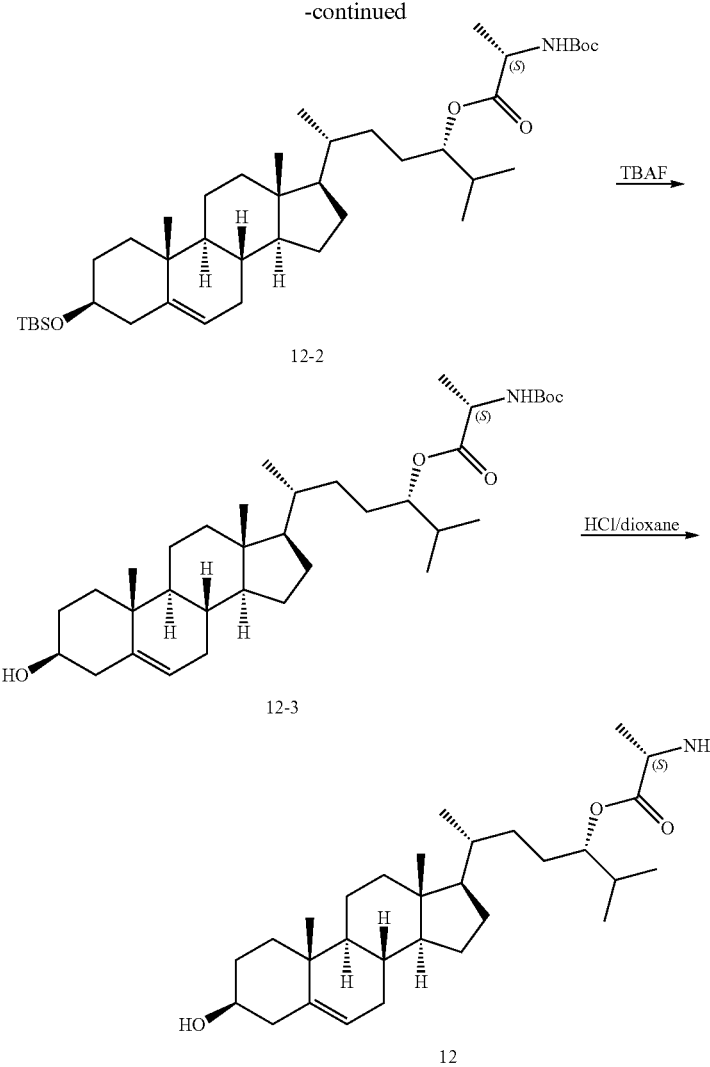

Synthesis of Compound 12-2

To a solution of Compound 1-1 (500 mg, 967 μmol) in DCM (5 mL) was added (S)-2-((tert-butoxycarbonyl)amino)propanoic acid (586 mg, 3.10 mmol), DCC (764 mg, 3.71 mmol), TEA (376 mg, 3.72 mmol), DMAP (151 mg, 1.24 mmol). The mixture was stirred at 30° C. for 3 hours. The mixture was washed by water (10 mL) and extracted with EtOAc (20 mL×2). The combined organic layer was dried over $Na_2SO_4$, filtered and concentrated to give a residue, which was diluted with water (15 mL). The suspension was heated at 60° C. for 30 minutes. The mixture was filtered to give Compound 12-2 (579 mg, 1.00 mmol) as an off-white solid. $^1$H NMR (400 MHz, $CDCl_3$) δ 5.31 (d, 1H), 5.19 (s, 1H), 5.08 (d, 1H), 4.79-4.62 (m, 1H), 4.38-4.06 (m, 1H), 3.56-3.39 (m, 1H), 2.35-2.10 (m, 2H), 2.08-1.90 (m, 2H), 1.90-1.66 (m, 5H), 1.65-1.32 (m, 21H), 1.30-0.79 (m, 28H), 0.66 (s, 3H), 0.17-0.01 (m, 6H).

Synthesis of Compound 12-3

To a solution of Compound 12-2 (300 mg, 435 μmol) was added TBAF/THF (5 mL, 1 M). The mixture was stirred at 23-25° C. for 30 minutes. The mixture was diluted with water (20 mL) and extracted by EtOAc (20 mL×2). The combined organic layer was dried over $Na_2SO_4$, filtered and concentrated to give a residue, which was purified by SFC ((Column: AD (250 mm*30 mm, 5 um), Condition: Base-ETOH, Begin: B 25% FlowRate (ml/min): 70) to give Compound 12-3 (392 mg) as an off-white solid. $^1$H NMR (400 MHz, $CDCl_3$) δ 5.53-5.20 (m, 1H), 5.09 (d, 1H), 4.86-4.57 (m, 2H), 4.30 (t, 1H), 3.84-3.35 (m, 1H), 2.52-2.17 (m, 2H), 2.04-1.92 (m, 2H), 1.89-1.75 (m, 4H), 1.69-0.82 (m, 42H), 0.67 (s, 3H).

Synthesis of Compound 12

Compound 12-1 (300 mg, 522 μmol) was added to HCl/dioxane (3 ml, 4M). The mixture was stirred at 25-27° C. for 1 hour. The mixture was filtered and washed with MTBE (5 ml×2), dried in vacuum to give an off-white solid. The residue was dissolved in water/MeCN (5 mL/1 mL) and lyophilized 3 times to removal residual solvents to give Compound 12-2 (90 mg, 34% yield) as an off white solid. $^1$H NMR (400 MHz, MeOD) δ 5.36 (d, 1H), 4.95-4. 4.70 (m, 3H), 3.80-3.70 (m, 1H), 3.46-3.36 (m, 1H), 2.28-2.16 (m, 2H), 2.10-1.75 (m, 6H), 1.76-1.61 (m, 2H), 1.62-1.39 (m, 11H), 1.38-1.25 (m, 1H), 1.25-1.07 (m, 4H), 1.04 (s, 3H), 1.01-0.91 (m, 10H), 0.74 (s, 3H). LCMS Rt=0.991 min in 2.0 min chromatography, 30-90 AB, MS ESI calcd. for $C_{30}H_{51}NO_3Na$ [M+Na]$^+$496.39, found 496.3.

Example 13. Synthesis of Compound 13

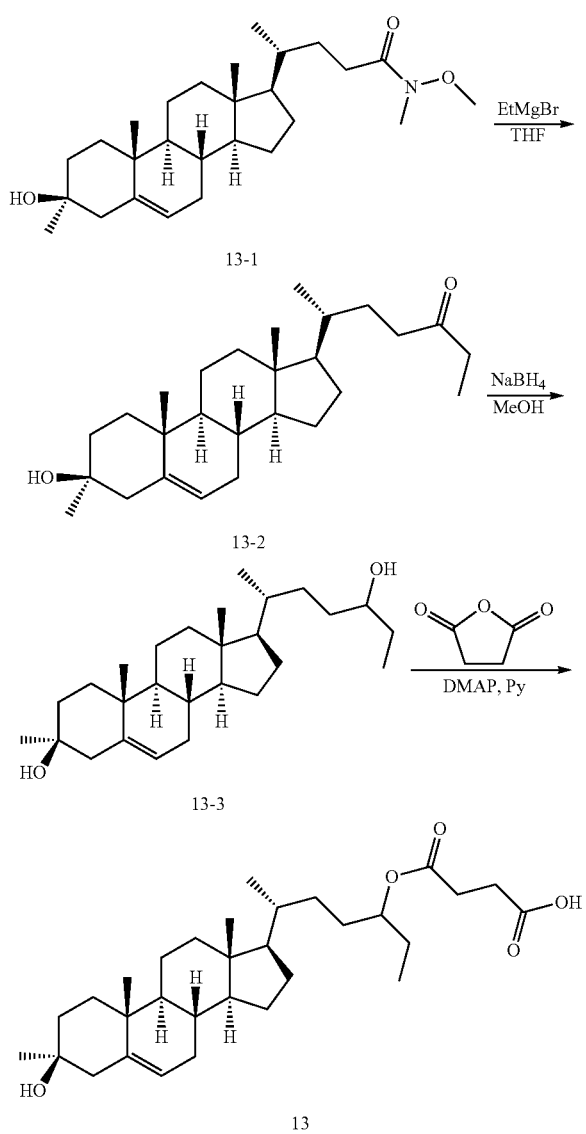

Step 1.

To a solution of 13-1 (7.0 g, 16.2 mmol) in THF (70 mL) was added dropwise ethylmagnesium bromide (26.9 mL, 80.9 mmol, 3M in $Et_2O$) at 0° C. under nitrogen atmosphere. The reaction mixture was stirred at 25° C. for 12 h. TLC showed the starting material was consumed completely. The mixture was quenched with saturated aqueous $NH_4Cl$ (100 mL) and extracted with EtOAc (200 mL×2). The combined organic phase was washed with brine (200 mL), dried over anhydrous $Na_2SO_4$, concentrated in vacuum. The residue was purified by column chromatography on silica gel (PE/EtOAc=20/1) to afford 13-2 (500 mg, 7.7%) as white solid. $^1$H NMR (400 MHz, CDCl3) δ 5.30-5.28 (m, 1H), 2.42-2.39 (m, 5H), 1.98-1.63 (m, 8H), 1.53-1.25 (m, 16H), 1.23-0.84 (m, 28H), 0.66 (s, 3H).

Step 2.

To a solution of 13-2 (500 mg, 1.24 mmol) in MeOH (10 mL) was added $NaBH_4$ (93.8 mg, 2.48 mmol) in portions. The reaction mixture was stirred at 25° C. for 2 h. After TLC showed the starting material was consumed and a new spot was produced. The reaction mixture was quenched with saturated aqueous $NH_4Cl$ (10 mL), extracted with EtOAc (30 mL×2). The combined organic phase was washed with brine (30 mL), concentrated in vacuum. The residue was purified by column chromatography on silica gel (PE/EtOAc=20/1) to afford 13-3 (500 mg, crude), which was purified by prep-HPLC to afford the pure 13-3 (60 mg, 12%) as white solid.

$^1$H NMR (400 MHz, CDCl3) δ 5.29 (d, J=4.4 Hz, 1H), 3.48-3.47 (m, 1H), 2.42 (d, J=12.8 Hz, 1H), 2.02-1.57 (m, 12H), 1.57-0.92 (m, 26H), 0.67 (s, 3H).

Step 3.

To a solution of Compound 13-3 (200 mg, 496 µmol) in pyridine (2 mL) was added DMAP (30.3 mg, 248 µmol) and dihydrofuran-2,5-dione (199 mg, 1.98 mmol). The mixture was stirred at 25-27° C. for 16 hr. The reaction mixture was washed by aqueous sat.$NH_4Cl$ (3 ml) and extracted with ethyl acetate (2 mL×2). The combined organic layer was concentrated in vacuum. The residue was purified by silica gel chromatography (PE/EtOAc=1/1) to afford Compound 13 (42 mg, 17% yield for mixture of diastereomers) as an off-white solid. $^1$H NMR (400 MHz, CDCl$_3$) δδ 5.35-5.22 (m, 1H), 4.87-4.70 (m, 1H), 2.79-2.54 (m, 4H), 2.42 (d, 1H), 2.09-1.91 (m, 3H), 1.89-1.64 (m, 3H), 1.64-1.30 (m, 13H), 1.32-0.76 (m, 21H), 0.67 (s, 3H). LCMS Rt=2.265 min in 3.0 min chromatography, 10-80 AB, MS ESI calcd. for $C_{31}H_{50}O_5Na$ [M+Na]$^+$525.37, found 525.3.

Example 14. Synthesis of Compound 14

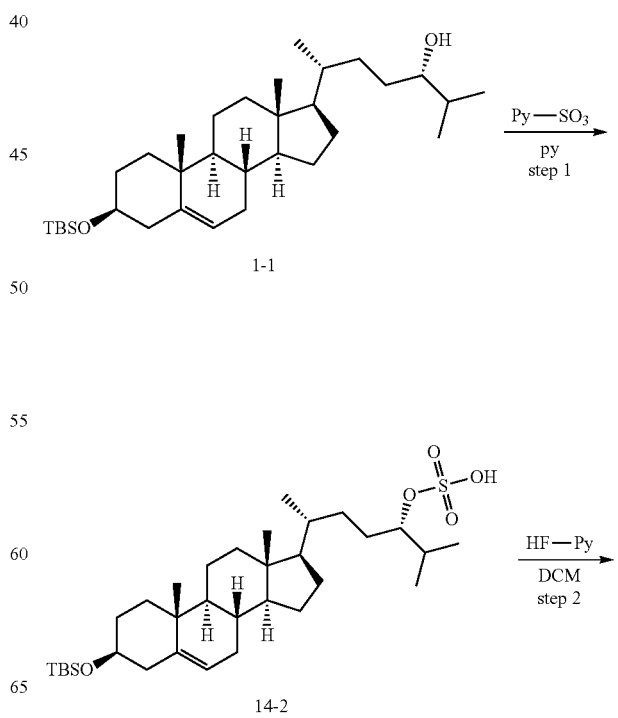

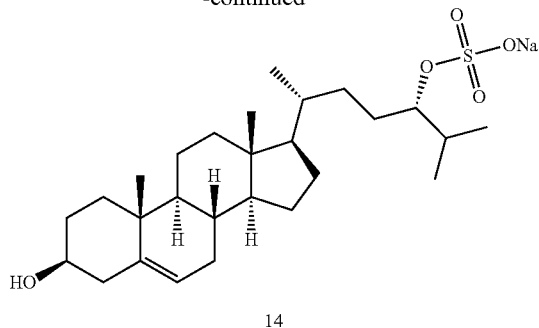

14

Synthesis of Compound 14-2

To a solution of Compound 1-1 (0.3 g, 0.58 mmol) in pyridine (2 mL) was added Py-SO$_3$ (276 mg, 1.74 mmol). The mixture was stirred at 40° C. for 16 hours. The mixture was concentrated and the residue was diluted with NaOH (20 mL, 3% in water). The mixture was extracted with PE (10 mL) and the organic layer was separated. The aqueous layer was extracted with BuOH (2×15 mL). The combined organic phase was dried over Na$_2$SO$_4$, filtered and concentrated to give Compound 14-2 (400 mg, crude) as yellow solid. $^1$H NMR (400 MHz, MeOD) δ 5.34-5.33 (m, 1H), 4.14-4.11 (m, 1H), 3.58-3.54 (m, 1H), 2.30-0.85 (m, 48H), 0.74 (s, 3H), 0.08 (s, 6H).

Synthesis of Compound 14

To a solution of Compound 14-2 (200 mg, 0.335 mmol) in DCM (5 ml) was added HF-Py (2 mL). The mixture was stirred at 15° C. for 16 hours. The reaction mixture was diluted with NaOH solution (10 mL, 3% in water) and extracted with DCM (2×5 mL). The combined organic layer was washed with NaOH solution (10 mL, 3% in water), separated, dried over Na$_2$SO$_4$, filtered and concentrated to give a residue, which was purified by combi-flash (PE: EA=100%-60%, DCM: MeOH=100%-90%) to give 50 mg of Compound 14 as colorless oil. The oil was crystallized from H$_2$O to give Compound 14 (10 mg, 6%) as an off-white solid. $^1$H NMR (400 MHz, MeOD) δ 5.36-5.35 (m, 1H), 4.63 (s, 1H), 4.17-4.13 (m, 1H), 3.43-3.38 (m, 1H), 2.24-2.20 (m, 2H), 2.15-0.85 (m, 37H), 0.74 (s, 3H). LCMS t$_R$=1.271 min in 2 min chromatography, 10-80AB_ELSD, MS ESI calcd. for C$_{27}$H$_{45}$O$_4$S [M+H–H$_2$O]$^+$465, found 465.

Example 16. Synthesis of Compounds 16 and 17

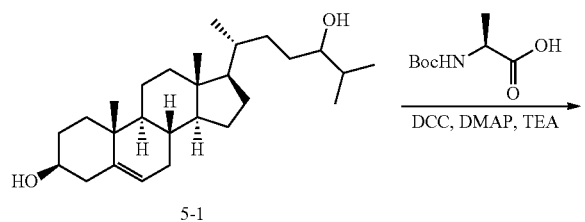

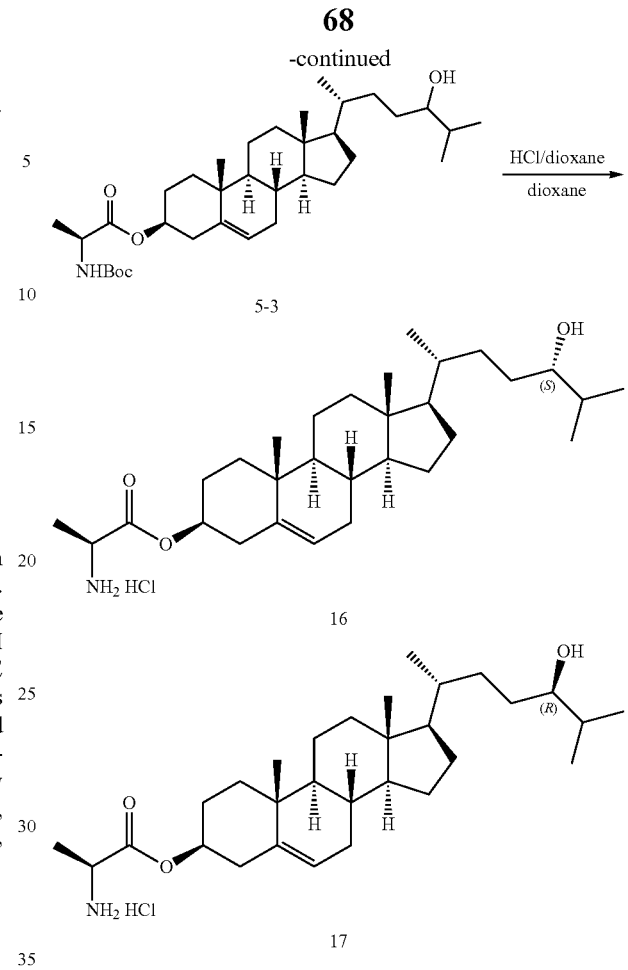

Synthesis of Compound 5-3

To a solution of Compound 5-1 (1.5 g, 3.72 mmol), Boc-Ala-OH (703 mg, 3.72 mmol), DMAP (45.4 mg, 0.37 mmol), TEA (376 mg, 3.72 mmol) in DCM (20 mL) was added DCC (767 mg, 3.72 mmol) at 15° C. The mixture was stirred at 15° C. for 20 hrs. The reaction mixture was filtered and the filtrate was concentrated in vacuum to give a crude product, which was purified by flash column (EtOAc in PE, 0-30% in 60 minutes) to give Compound 5-3 (600 mg, 28%).

Synthesis of Compounds 16 and 17

To a solution of Compound 5-3 (600 mg) in dioxane (4 mL) was added HC N (2 mL, 4 M in dioxane) at 15° C. The mixture was stirred at 15° C. for 16 hrs. MTBE (15 mL) was added and an off-white solid was produced. The mixture was filtered. The filtered cake was washed with MTBE, concentrated in vacuum to give an off-white solid (600 mg), which was purified by prep. HPLC (Column: Phenomenex Gemini 150*25 mm*10 um; condition: water (0.05% HCl)—ACN, 50-60% B in 10 mins, 100% B Hold Time (min): 4; FlowRate (ml/min): 25) to give Compound 16 (9 mg, 11%) and Compound 17 (33 g, 40%).

Compound 16:
$^1$H NMR (400 MHz, DMSO-d$_6$) δ 8.40-8.30 (br, 3H), 5.45-5.30 (m, 1H), 4.70-4.50 (m, 1H), 4.23-4.10 (m, 1H), 4.10-3.98 (m, 1H), 3.10-3.00 (m, 1H), 2.40-2.20 (m, 2H), 2.03-1.71 (m, 5H), 1.67-10.88 (m, 28H), 0.86-0.78 (m, 6H), 0.66 (s, 3H). LCMS Rt=1.014 min in 2.0 min chromatography, 30-90 AB_E, MS ESI calcd. for $C_{27}H_{45}O$ [M+H-AlaOH]$^+$385, found 385.

Compound 17:

$^1$H NMR (400 MHz, DMSO-d$_6$) δ 8.40-8.30 (br, 3H), 5.45-5.30 (m, 1H), 4.70-4.50 (m, 1H), 4.23-4.10 (m, 1H), 4.10-3.98 (m, 1H), 3.10-3.00 (m, 1H), 2.40-2.20 (m, 2H), 2.03-1.71 (m, 5H), 1.67-0.88 (m, 28H), 0.86-0.78 (m, 6H), 0.66 (s, 3H). LCMS Rt=1.011 min in 2.0 min chromatography, 30-90 AB_E, MS ESI calcd. $C_{27}H_{45}O$ [M+H-AlaOH]$^+$385, found 385.

Example 17. Synthesis of Compound 18

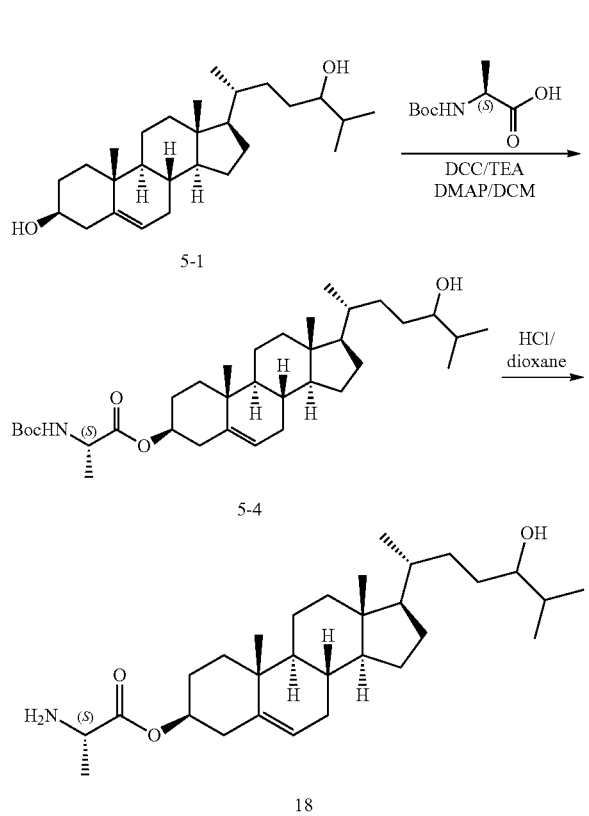

Synthesis of Compound 5-4

To a solution of Compound 5-1 (100 mg, 248 μmol) in DCM (2 mL) at 13~18° C. was added N,N-dimethylpyridin-4-amine (3 mg, 24.5 μmol), triethylamine (25 mg, 247 μmol), (S)-2-((tert-butoxycarbonyl)amino)propanoic acid (47 mg, 248 μmol) and N,N'-methanediylidenedicyclohexanamine (51 mg, 247 μmol). The reaction was stirred over 16 hrs at 20° C. The reaction was filtered and filtrate was concentrated. The residue was purified by silica gel chromatography (PE/EtOAc=20/1) to give the desired product (45 mg, 24%) as a solid.

Synthesis of Compound 18

To a solution of Compound 5-4 (45 mg, 78.4 μmol) in dioxane (1 mL) was added HCl/dioxane (4 M, 1 mL) at 15-28° C. The reaction mixture was stirred for 3 hrs. and then 5 mL of sat. NaHCO$_3$ was added so the reaction was at pH=9. The mixture was extracted with EtOAc (3×10 mL). The combined organic layer was washed with brine (10 mL), dried over Na$_2$SO$_4$, filtered and concentrated. The residue was purified by silica gel chromatography (DCM/MeOH=15/1) to give Compound 18 (3.2 mg, 8%) as an off-white solid. $^1$H NMR (CDCl$_3$, 400 MHz): δ 5.40-5.39 (m, 1H), 4.67-4.64 (m, 1H), 3.56-3.54 (m, 1H), 3.34-3.33 (m, 1H), 2.35-2.33 (m, 2H), 2.05-1.90 (m, 2H), 1.88 (m, 3H), 1.67-0.91 (m, 37H), 0.70 (s, 3H). LCMS Rt=1.866 min in 3.0 min chromatography, 10-80 AB, MS ESI calcd. for $C_{27}H_{45}O$ [M+H-AlaOH]$^+$385, found 385.

Example 18. Synthesis of Compound 19

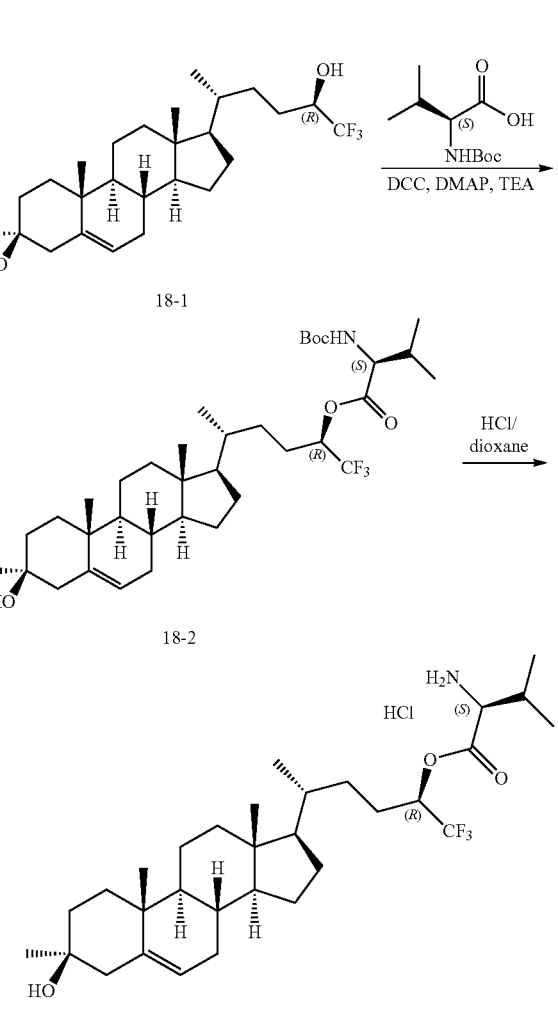

Synthesis of Compound 18-2

To a solution of Compound 18-1 (100 mg, 0.225 mmol; synthesized as described in Martinez et al., WO2014/160480) in DCM (1 mL) was added DMAP (8.2 mg, 0.0675 mmol), Boc-Vla-OH (146 mg, 0.675 mmol), TEA (68.3 mg, 0.675 mmol) and DCC (139 mg, 0.675 mmol). The mixture was stirred at 25° C. for 16 hours. The mixture was concentrated under vacuum, purified by column chromatography on silica gel (PE/EtOAc=15:1) to give Compound 18-2 (80 mg, 55%) as an off-white solid.

$^1$H NMR (400 MHz, CDCl$_3$) δ 5.35-5.20 (m, 2H), 5.00-4.90 (m, 1H), 4.38-4.25 (m, 1H), 2.48-2.37 (m, 1H), 2.25-2.15 (m, 1H), 2.02-1.90 (m, 3H), 1.85-0.85 (m, 46H), 0.67 (s, 3H).

Synthesis of Compound 19

To a solution of Compound 18-2 (70 mg, 0.124 mmol) in dioxane (0.5 mL) was added HCl/dioxane (1 mL, 4 M). The mixture was stirred at 25° C. for 2 hours and an off-white solid was formed. To the reaction mixture was added MTEB (10 mL) and the reaction was filtered. The solid was washed with MTEB (10 mL) and then dissolved in MeOH (10 mL). The MeOH solution was concentrated in vacuum to give Compound 19 (55.6 mg, 77%) as an off-white solid. $^1$H NMR (400 MHz, methanol-d4) δ 5.60-5.50 (m, 1H), 5.34-5.25 (m, 1H), 4.16 (d, J=4.0 Hz, 1H), 2.48-2.30 (m, 2H), 2.05-1.40 (m, 16H), 1.35-0.90 (m, 23H), 0.74 (s, 3H). LCMS Rt=0.970 min in 2.0 min chromatography, 30-90 AB, MS ESI calcd. for C$_{31}$H$_{51}$F$_3$NO$_3$ [M+H]$^+$ 542, found 542.

Example 19. Synthesis of Compound 20

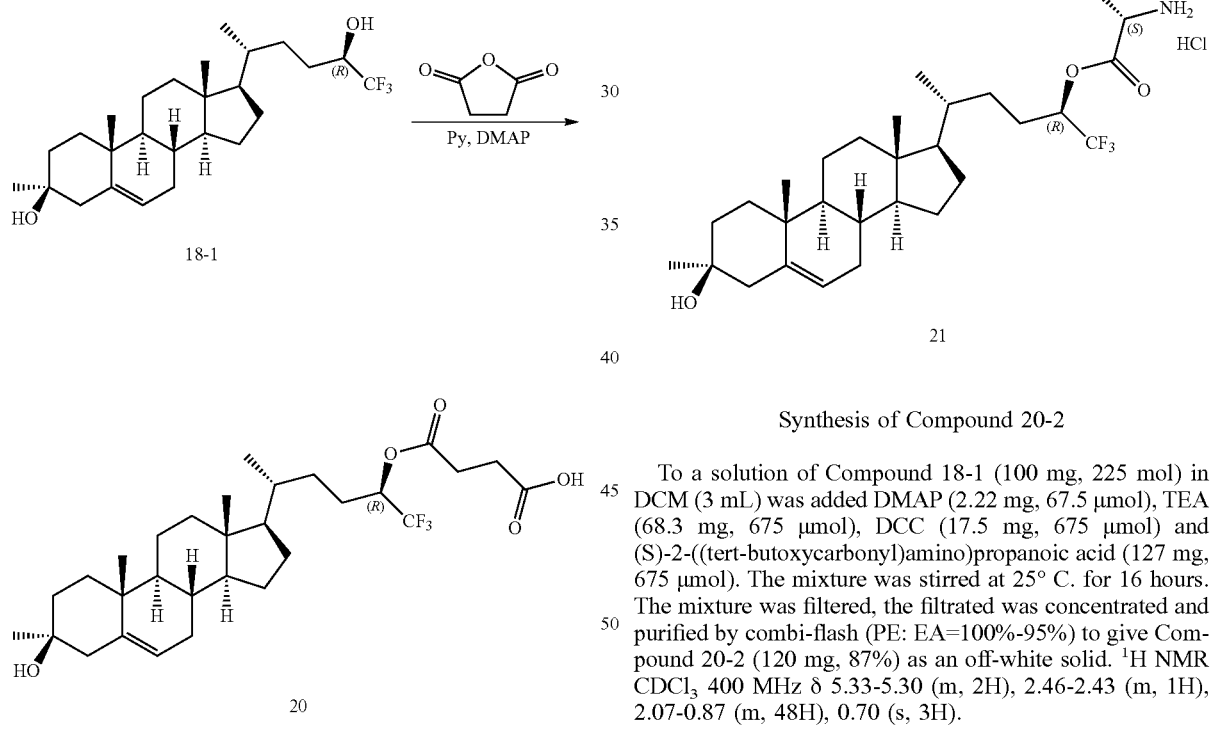

To a solution of Compound 18-1 (50 mg, 0.122 mmol) in pyridine (1 mL) was added DMAP (6.8 mg, 0.056 mmol) and dihydrofuran-2,5-dione (33.6 mg, 336 mmol). The mixture was stirred at 25° C. for 16 hours. The mixture was concentrated under vacuum, purified by column chromatography on silica gel (PE/EtOAc=1:1) to give Compound 20 (14.1 mg, yield 23%) as an off-white solid. $^1$H NMR (400 MHz, CDCl$_3$) δ 5.35-5.25 (m, 2H), 2.78-2.65 (m, 4H), 2.46-2.37 (m, 1H), 2.05-1.90 (m, 4H), 1.70-0.90 (m, 30H), 0.67 (s, 3H). LCMS Rt=1.226 min in 2.0 min chromatography, 30-90 AB, MS ESI calcd. for C$_{30}$H$_{44}$F$_3$O$_4$ [M+H–H$_2$O]$^+$525, found 525.

Example 20. Synthesis of Compound 21

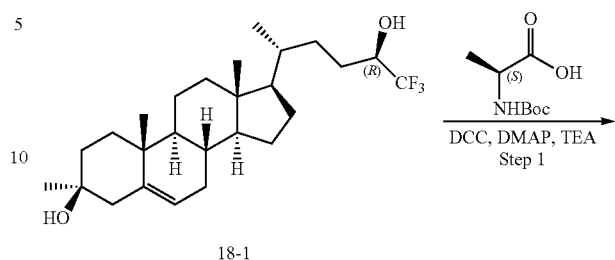

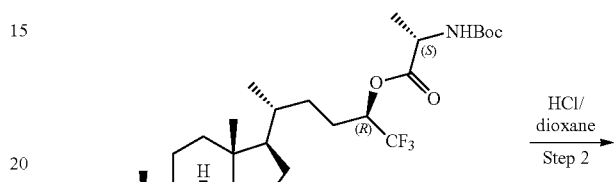

Synthesis of Compound 20-2

To a solution of Compound 18-1 (100 mg, 225 mol) in DCM (3 mL) was added DMAP (2.22 mg, 67.5 μmol), TEA (68.3 mg, 675 μmol), DCC (17.5 mg, 675 μmol) and (S)-2-((tert-butoxycarbonyl)amino)propanoic acid (127 mg, 675 μmol). The mixture was stirred at 25° C. for 16 hours. The mixture was filtered, the filtrated was concentrated and purified by combi-flash (PE: EA=100%-95%) to give Compound 20-2 (120 mg, 87%) as an off-white solid. $^1$H NMR CDCl$_3$ 400 MHz δ 5.33-5.30 (m, 2H), 2.46-2.43 (m, 1H), 2.07-0.87 (m, 48H), 0.70 (s, 3H).

Synthesis of Compound 21

To a solution of Compound 20-2 (120 mg, 195 μmol) was added HCl/dioxane (4N, 1 mL). The mixture was stirred at 25° C. for 0.5 hour. To the mixture was added MTBE (3 mL) and stirred at 25° C. for 10 minutes. The mixture was filtered. The solid was washed with MTBE (3 mL), dried in vacuum to give Compound 21 (60 mg, 56%). $^1$H NMR (400 MHz, MeOD) δ 5.52-5.51 (m, 1H), 5.32-5.31 (m, 1H), 4.30-4.26 (m, 1H), 2.46-2.43 (m, 1H), 2.05-1.00 (m, 36H), 0.76 (s, 3H). LCMS Rt=0.940 min in 2 min chromatography, 30-90AB, MS ESI calcd. for C$_{29}$H$_{47}$F$_3$NO$_3$ [M+H]$^+$ 514, found 514.

Example 21. Synthesis of Compound 22

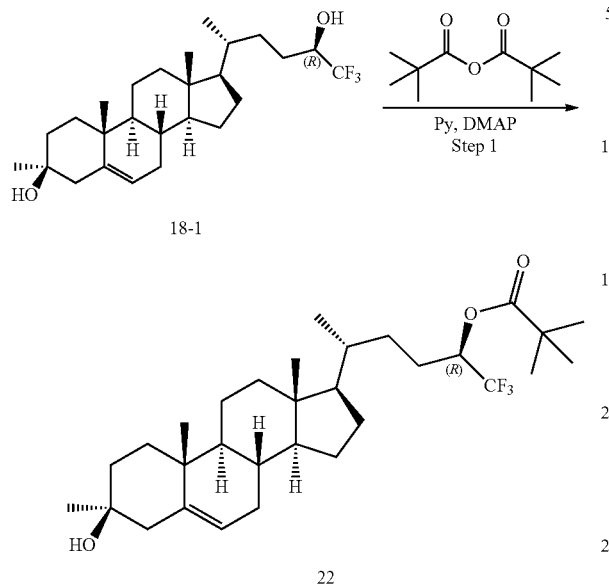

Step 1.

To a mixture of Compound 18-1 (50 mg, 112 μmol) and DMAP (6.84 mg, 56.0 μmol) in pyridine (2 mL) was added pivalic anhydride (104 mg, 560 μmol) in one portion at 20° C. The mixture was stirred at 60° C. for 16 hrs. The resulting mixture was concentrated to give a residue, which was diluted with water (30 mL) and extracted with EtOAc (2×15 mL). The combined organic layers were dried over Na$_2$SO$_4$, filtered and concentrated in vacuum to give a crude product, which was purified by silica gel chromatography (PE/EtOAc=8/1) to give Compound 22 (14 mg, 24%) as an off-white solid. The reaction was conducted for a second time to give 30 mg of impure product. The 2 batches of product (30 mg) were combined and triturated with hexane (5 mL) to give Compound 22 (23 mg, 52%) as an off-white solid. $^1$H NMR (400 MHz, CDCl$_3$) δ 5.33-5.19 (m, 2H), 2.45-2.38 (m, 1H), 2.03-1.91 (m, 3H), 1.86-0.80 (m, 40H), 0.60 (s, 3H). LCMS t$_R$=1.575 min in 2 min chromatography, 30-90AB_ELSD, MS ESI calcd. for C$_{31}$H$_{48}$F$_3$O$_2$ [M+H–H$_2$O]$^+$509, found 509.

Example 21. Synthesis of Compound 23

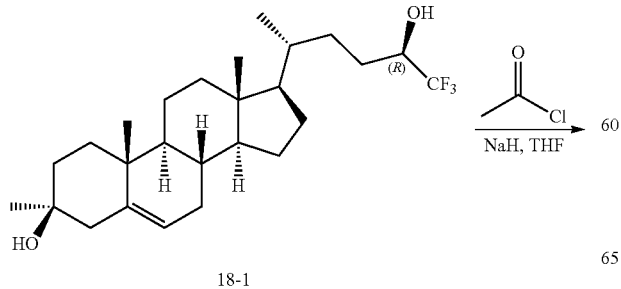

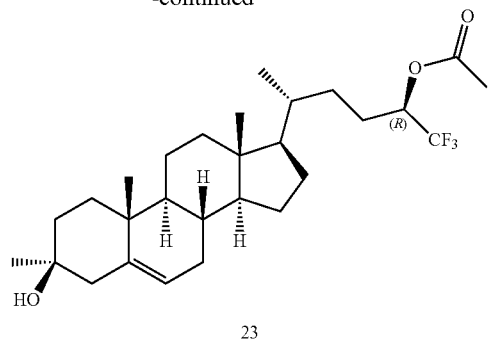

Step 1.

To a solution of Compound 18-1 (100 mg, 0.225 mmol) in THF (5 mL) was added NaH (22.3 mg, 0.562 mmol, 60%) under N$_2$ at 0° C. The mixture was stirred at 20° C. for 30 minutes. Acetyl chloride (35.3 mg, 0.45 mmol) was added. The reaction solution was stirred at 20° C. for 30 minutes. The mixture was quenched with Sat. NH$_4$Cl (10 mL) and extracted with MTBE (3×5 mL). The combined organic phase was washed with brine, dried over Na$_2$SO$_4$, filtered, concentrated and purified by combi-flash (0-8% of EtOAc in PE) to give Compound 23 (39 mg, 35%) as an off-white solid. $^1$H NMR (400 MHz, CDCl$_3$) δ 5.30-5.29 (m, 2H), 2.48-2.38 (m, 1H), 2.14 (s, 3H), 2.05-1.95 (m, 3H), 1.94-1.56 (m, 6H), 1.54-1.47 (m, 8H), 1.45-0.92 (m, 17H), 0.59 (s, 3H). LCMS t$_R$=1.383 min in 2 min chromatography, 30-90AB_ELSD, MS ESI calcd. for C$_{28}$H$_{42}$F$_3$O$_2$ [M+H–H$_2$O]$^+$467, found 467.

Example 22. Synthesis of Compound 24

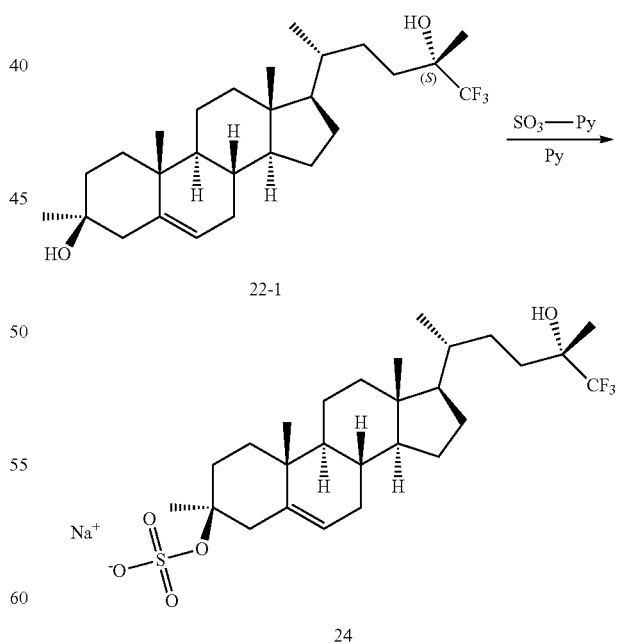

Step 1.

To a solution of Compound 22-1 (500 mg, 1.09 mmol; synthesized as described in Martinez et al., WO2014/160480, [00199]) in pyridine (3 mL) was added SO$_3$—Py (519 mg, 3.27 mmol). The mixture was stirred at 50° C. for 1 h. The mixture was diluted with water (10 mL) and extracted with DCM (2×10 mL). The combined organic phase was washed with water (10 mL). To the organic phase was added dropwise NaOH solution (2 mL, 3% in water) with stirring and some white solid appeared. The solid was collected by filtration and washed with DCM (10 mL) and water (10 mL). The solid was purified by preparative-HPLC ((column: DuraShell 150*25 mm*5 um), gradient: 35-60% B (A=water (10 mM NH₄HCO₃), B=ACN), flow rate: 30 mL/min). After the purification was finished, to the combined eluent was added DCM (10 mL) and added dropwise NaOH solution (2 mL, 3% in water). Compound 24 (62 mg, 10%) was obtained by collection and lyophilization to give an off-white solid. $^1$H NMR (400 MHz, CD₃OD) δ 5.36-5.35 (m, 1H), 2.88-2.85 (m, 1H), 2.35-2.31 (m, 1H), 2.21-2.01 (m, 2H), 2.00-1.75 (m, 4H), 1.70-1.43 (m, 10H), 1.41 (s, 3H), 1.38-1.30 (m, 1H), 1.27 (s, 3H), 1.22-1.10 (m, 5H), 1.09-1.02 (m, 4H), 1.00-0.92 (m, 4H), 0.75 (s, 3H). LCMS Rt=1.683 min in 2 min chromatography, 10-80CD_ELSD, MS ESI calcd. for $C_{27}H_{42}F_3O_5S$ [M]⁻ 535, found 535.

Example 23. Synthesis of Compound 25

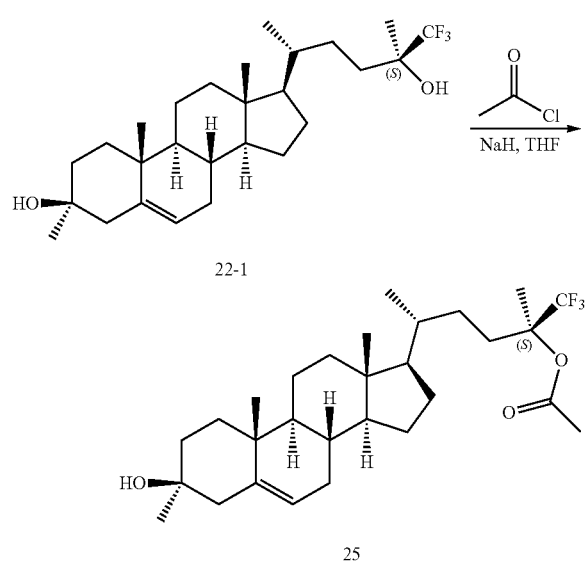

Step 1.

To a solution of Compound 22-1 (500 mg, 1.09 mmol) in THF (10 mL) was added NaH (108 mg, 2.72 mmol, 60%) under N₂ at 0° C. The mixture was stirred at 20° C. for 30 minutes. Then acetyl chloride (171 mg, 2.18 mmol) was added. The reaction solution was stirred at 20° C. for 1 h. The mixture was quenched with Sat. NH₄Cl (10 mL) and extracted with EtOAc (3×10 mL). The combined organic phase was dried over Na₂SO₄, filtered, concentrated and purified by combi-flash (0-30% of EtOAc in PE, 60 mins) to give Compound 25 (26 mg, 5%) as an off-white solid. $^1$H NMR (400 MHz, CDCl₃) δ 5.35-5.25 (m, 1H), 2.50-2.40 (m, 1H), 2.30-2.10 (m, 1H), 2.06 (s, 3H), 2.00-1.60 (m, 12H), 1.53-1.35 (m, 7H), 1.30-0.90 (m, 17H), 0.67 (s, 3H). LCMS Rt=3.743 min in 7.0 min chromatography, 50-100 AB_E, MS ESI calcd. for $C_{29}H_{44}F_3O_2$[M+H-H₂O]⁺481, found 481.

Example 24. Synthesis of Compound 26

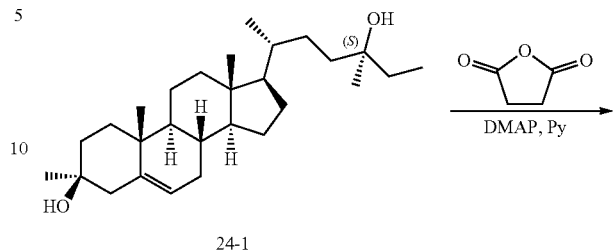

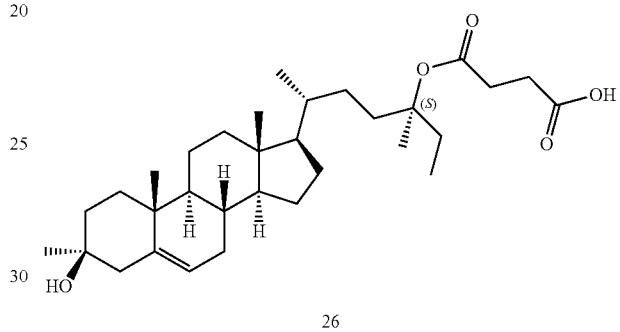

Step 1.

To a solution of Compound 24-1 (100 mg, 239 μmol; synthesized as described in Martinez et al., WO2014/160480, [00210]) in pyridine (2 mL) was added DMAP (30.5 mg, 478 μmol) and dihydrofuran-2,5-dione (119 mg, 1.19 mmol). The mixture was stirred at 60° C. for 40 hrs. The reaction mixture was washed by Sat.NH₄Cl (3 ml) and extracted with ethyl acetate (2×2 ml). The combined organic layer was concentrated in vacuum. The residue was purified by silica gel chromatography (petroleum PE:EtOAc=10:1) to afford Compound 26 (35 mg, yield 28%) as an off-white solid. $^1$H NMR CDCl₃ 400 MHz δ 5.35-5.30 (m, 1H), 2.64-2.61 (m, 5H), 2.58-2.56 (m, 1H), 2.01-0.86 (m, 42H), 0.67 (s, 3H). LCMS Rt=1.341 min in 2 min chromatography, 30-90AB, MS ESI calcd. for $C_{28}H_{45}$ [M+H-H₂O-HOOCCH₂CH₂COOH]⁺381, found 381.

Example 25. Synthesis of Compounds 27 and 28

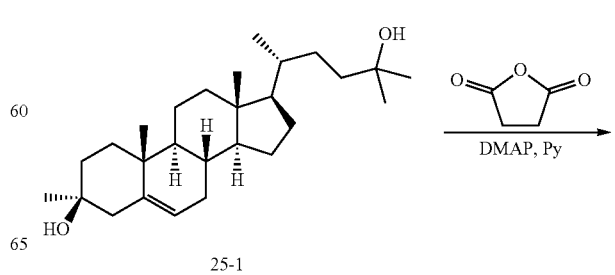

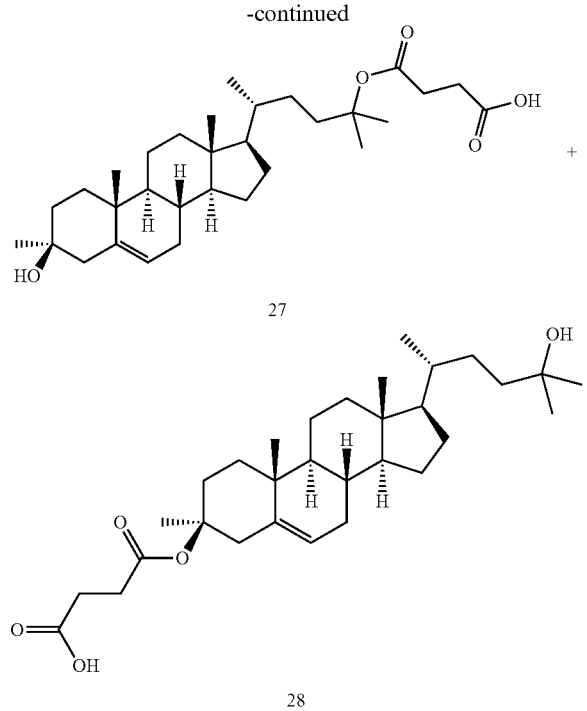

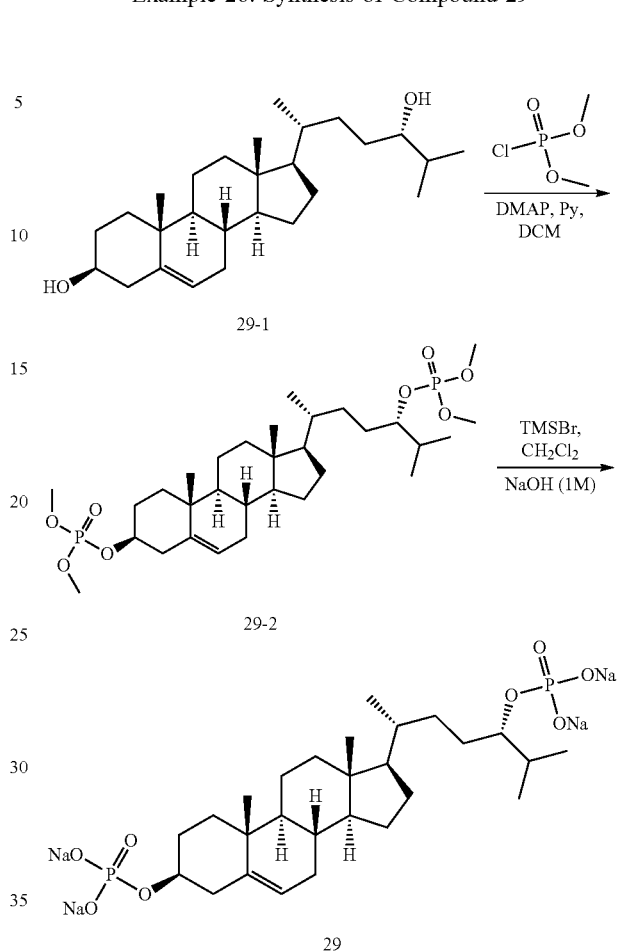

Example 26. Synthesis of Compound 29

Step 1.

To a solution of Compound 25-1 (900 mg, 2.23 mmol) in pyridine (20 mL) was added dihydrofuran-2,5-dione (1.11 g, 11.1 mmol) and DMAP (272 mg, 2.23 mmol). The mixture was stirred at 80° C. for 96 hrs. The reaction solution was quenched with sat.NH$_4$Cl (25 mL) and extracted with EtOAc (3×10 mL). The combined organic phase was dried over Na$_2$SO$_4$, filtered, concentrated. The reaction mixture was separated by combi-flash (0-10% of (MeOH: EtOAc, v:v=1:20) in DCM: PE, v:v=1:2) and the recycled starting material was reused in this experiment (this procedure was repeat for 4 times). The combined impure product was purified by preparative-HPLC (column: Boston Green ODS 150*30 5u), gradient: 65-95% B (A=0.05% HCl/H$_2$O, B=MeCN), flow rate: 75 mL/min) to give Compound 27 (40 mg, 34%) and Compound 28 (55 mg, 4%) as off-white solids.

27: $^1$H NMR (400 MHz, CDCl$_3$) δ 5.30-5.29 (m, 1H), 2.65-2.55 (m, 4H), 2.45-2.35 (m, 1H), 2.05-1.92 (m, 3H), 1.90-1.76 (m, 3H), 1.75-1.53 (m, 5H), 1.52-1.46 (m, 3H), 1.45-1.40 (m, 7H), 1.39-1.30 (m, 2H), 1.29-1.20 (m, 1H), 1.19-1.15 (m, 2H), 1.14-1.10 (m, 4H), 1.09-1.02 (m, 2H), 1.01-0.94 (m, 4H), 0.93-0.86 (m, 5H), 0.67 (s, 3H). LCMS Rt=1.268 min in 2.0 min chromatography, 30-90AB_ELSD, MS ESI calcd. for C$_{27}$H$_{43}$ [M+H−H$_2$O−(CH$_2$COOH)$_2$]$^+$ 367, found 367. HRMS MS ESI calcd. for C$_{31}$H$_{49}$O$_5$[M−H]$^-$ 501.3585, found 501.3575. 28: $^1$H NMR (400 MHz, CDCl$_3$) δ 5.30-5.29 (m, 1H), 2.66-2.52 (m, 5H), 2.38-2.32 (m, 1H), 2.08-1.77 (m, 6H), 1.76-1.71 (m, 1H), 1.70-1.52 (m, 3H), 1.51-1.40 (m, 10H), 1.39 (s, 3H), 1.38-1.18 (m, 6H), 1.17-1.11 (m, 4H), 1.10 (s, 3H), 1.09-0.95 (m, 1H), 0.94-0.88 (m, 3H), 0.68 (s, 3H). LCMS Rt=1.280 min in 2.0 min chromatography, 30-90AB_ELSD, MS ESI calcd. for C$_{27}$H$_{43}$ [M+H−H$_2$O−(CH$_2$COOH)$_2$]$^+$367, found 367. HRMS MS ESI calcd. for C$_{31}$H$_{49}$O$_5$[M−H]$^-$ 501.3585, found 501.3597.

Step 1.

To a solution of Compound 29-1 (1.5 g, 3.72 mmol) in DCM (30 mL) was added DMAP (226 mg, 1.86 mmol) and Py (8.65 g, 111 mmol), followed by adding bimethyl phosphorochloridate (2.68 g, 18.6 mmol) dropwise under N$_2$. The reaction was stirred at 20° C. for 2 hrs. The mixture was quenched with sat.NaHCO$_3$ (100 mL) and extracted with DCM (3×40 mL). The combined organic phase was dried over Na$_2$SO$_4$, filtered, concentrated and purified by combi-flash (0-50% of EtOAc in PE/DCM (v/v=2/1)) to give Compound 29-2 (620 mg, 27%) as an off-white solid. $^1$H NMR (400 MHz, CDCl$_3$) δ 5.40-5.37 (m, 1H), 4.35-4.15 (m, 2H), 3.77 (s, 6H), 3.74 (s, 6H), 2.45-2.35 (m, 2H), 2.05-1.87 (m, 4H), 1.86-1.78 (m, 2H), 1.77-1.58 (m, 2H), 1.56-1.33 (m, 7H), 1.30-1.15 (m, 4H), 1.14-1.04 (m, 3H), 1.02 (s, 3H), 1.01-0.88 (m, 11H), 0.67 (s, 3H).

Step 2.

To a solution of Compound 29-2 (200 mg, 0.323 mmol) in DCM (5 mL) was added TMSBr (246 mg, 1.61 mmol) under N$_2$. The mixture was stirred at 20° C. for 16 hrs. The reaction mixture was adjusted to pH=9 with aq. NaOH (1.9 mL, 1 M) and the solid precipitated. The white solid was filtered and washed with CH$_2$Cl$_2$ (2 mL), water (2 mL), dried and lyophilized to give Compound 29 (68 mg, 37%) as an off-white solid. $^1$H NMR (400 MHz, MeOD) δ 5.40-5.37 (m, 1H), 4.10-3.90 (m, 2H), 2.48-2.30 (m, 2H), 2.08-1.85 (m, 7H), 1.70-1.58 (m, 10H), 1.35-1.25 (m, 1H), 1.20-1.04 (m, 5H), 1.02 (s, 3H), 1.00-0.96 (m, 7H), 0.95-0.88 (m, 3H), 0.71 (s, 3H). LCMS $t_R$=0.207 min in 3 min chromatography, 10-80CD_ELSD, MS ESI calcd. for $C_{27}H_{47}O_8P_2$ [M−4Na+ 4H−H]⁻ 561, found 561.

Example 27. Synthesis of Compound 30

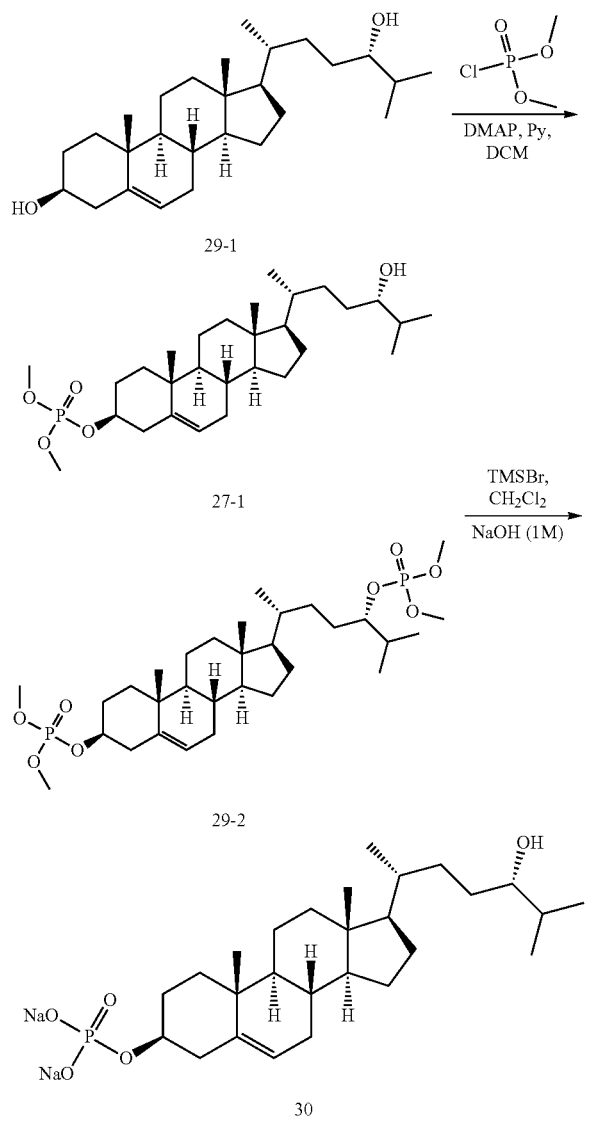

Step 1.

To a solution of 29-1 (1.5 g, 3.72 mmol) in DCM (30 mL) was added DMAP (226 mg, 1.86 mmol) and Py (8.65 g, 111 mmol), followed by adding bimethyl phosphorochloridate (2.68 g, 18.6 mmol) dropwise under $N_2$. The reaction was stirred at 20° C. for 2 hrs. The mixture was quenched with sat.NaHCO₃ (100 mL) and extracted with DCM (3×40 mL). The combined organic phase was dried over $Na_2SO_4$, filtered, concentrated and purified by combi-flash (0-50% of EtOAc in PE/DCM (v/v=2/1)) to give 27-1 (700 mg, 37%) as an off-white solid.

¹H NMR (400 MHz, CDCl₃) δ 5.40-5.37 (m, 1H), 4.28-4.15 (m, 1H), 3.80-3.70 (m, 6H), 3.35-3.25 (m, 1H), 2.45-2.40 (m, 2H), 2.02-1.90 (m, 3H), 1.89-1.76 (m, 2H), 1.75-1.58 (m, 2H), 1.56-1.33 (m, 8H), 1.30-1.15 (m, 7H), 1.14-0.96 (m, 5H), 0.95-0.88 (m, 10H), 0.67 (s, 3H).

Step 2.

To a solution of 27-1 (200 mg, 0.391 mmol) in DCM (5 mL) was added TMSBr (298 mg, 1.95 mmol). The mixture was stirred at 20° C. for 16 hrs. Another TMSBr (596 mg, 3.9 mmol) was added at 0° C. The mixture was stirred at 20° C. for 16 hrs. The mixture was adjusted with NaOH (1M in H₂O) to pH=9 and the solid was precipitated. The white solid was filtered and washed with CH₂Cl₂ (2 mL), water (2 mL), dissolved in MeOH (6 mL) and concentrated to give Compound 30 (16 mg, 8%) as an off-white solid. ¹H NMR (400 MHz, MeOD) δ 5.42-5.29 (m, 1H), 4.04-3.82 (m, 1H), 3.25-3.15 (m, 1H), 2.63-2.41 (m, 1H), 2.35-2.11 (m, 1H), 2.10-1.80 (m, 4H), 1.79-1.37 (m, 10H), 1.37-1.27 (m, 2H), 1.26-1.05 (m, 6H), 1.02 (s, 3H), 0.99-0.77 (m, 13H), 0.72 (s, 3H). LCMS $t_R$=1.311 min in 3 min chromatography, 10-80CD_ELSD, MS ESI calcd. for $C_{27}H_{46}O_5P$ [M−2Na+ 2H−H]⁻ 481, found 481.

Example 28. Alternative Synthesis of Compound 6

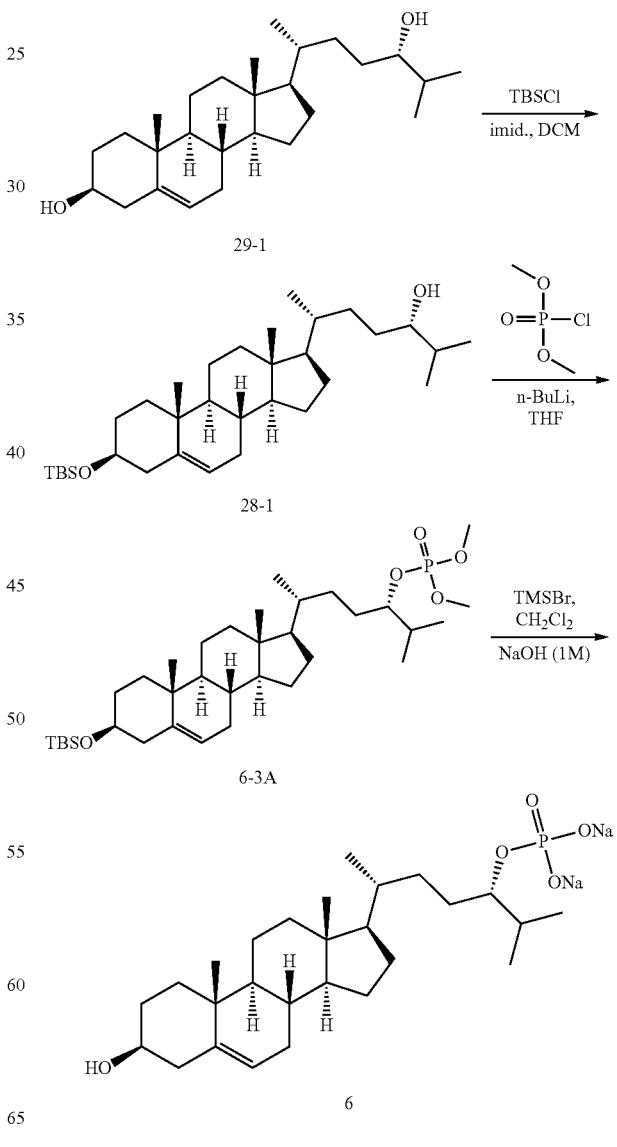

Step 1.

To a solution of 29-1 (1.4 g, 3.47 mmol) in DCM (25 mL) was added imidazole (471 mg, 6.94 mmol). A solution of TBSCl (1.39 g, 10.4 mmol) in DCM (5 mL) was added dropwise under $N_2$. The reaction was stirred at 20° C. for 16 hrs. The mixture was quenched with water (30 mL) and extracted with DCM (2×15 mL). The combined organic phase was dried over $Na_2SO_4$, filtered, concentrated and purified by combi-flash (0-5% of EtOAc in PE) to give 28-1 (1.5 g, 84%) as an off-white solid. $^1$H NMR (400 MHz, $CDCl_3$) δ 5.33-5.30 (m, 1H), 3.52-3.43 (m, 1H), 3.34-3.27 (m, 1H), 2.31-2.13 (m, 2H), 2.04-1.92 (m, 2H), 1.90-1.76 (m, 2H), 1.75-1.57 (m, 4H), 1.54-1.37 (m, 7H), 1.34-1.19 (m, 4H), 1.18-1.01 (m, 5H), 0.99 (s, 3H), 0.96-0.89 (m, 9H), 0.88-0.85 (m, 10H), 0.67 (s, 3H), 0.05 (s, 6H).

Step 2.

To a solution of 28-1 (900 g, 1.74 mmol) in THF (30 mL) was added n-BuLi (1.04 mL, 2.61 mmol, 2.5M in hexane) dropwise at −70° C. under $N_2$. The reaction solution was stirred at −70° C. for 30 minutes. Then dimethyl phosphorochloridate (502 mg, 3.48 mmol) was added dropwise. After addition, the mixture was stirred at 20° C. for 2 hrs. The reaction solution was quenched with sat.$NH_4Cl$ (50 mL) and extracted with DCM (2×30 mL). The combined organic phase was dried over $Na_2SO_4$, filtered, concentrated and purified by combi-flash (0-20% of EtOAc in PE) to give 6-3A (540 mg, 50%) as colorless oil. $^1$H NMR (400 MHz, $CDCl_3$) δ 5.33-5.29 (m, 1H), 4.23-4.15 (m, 1H), 3.81-3.71 (m, 6H), 3.53-3.43 (m, 1H), 2.32-2.22 (m, 1H), 2.18-1.64 (m, 9H), 1.60-1.33 (m, 11H), 1.31-1.06 (m, 5H), 0.99 (s, 3H), 0.97-0.90 (m, 10H), 0.89-0.85 (m, 8H), 0.67 (s, 3H), 0.05 (s, 6H).

Step 3.

To a solution of 6-3A (180 mg, 0.288 mmol) in DCM (5 mL) was added TMSBr (220 mg, 1.44 mmol). The mixture was stirred at 20° C. for 16 hrs. The mixture was adjusted with NaOH (1M in $H_2O$) to pH=9 and the solid was precipitated, which was filtered and washed with $CH_2Cl_2$ (2 mL), water (2 mL). The filter cake was dissolved in MeOH (6 mL) and concentrated to give Compound 6 (35 mg, 25%) as an off-white solid. $^1$H NMR (400 MHz, MeOD) δ 5.37-5.31 (m, 1H), 4.01-3.89 (m, 1H), 3.45-3.35 (m, 1H), 2.29-2.14 (m, 2H), 2.09-1.84 (m, 5H), 1.82-1.72 (m, 1H), 1.66-1.38 (m, 10H), 1.37-1.26 (m, 1H), 1.24-1.04 (m, 5H), 1.03-1.00 (m, 4H), 0.99-0.93 (m, 7H), 0.92-0.85 (m, 4H), 0.72 (s, 3H). LCMS $t_R$=1.370 min in 3 min chromatography, 10-80CD_ELSD, MS ESI calcd. for $C_{27}H_{46}O_5P$ [M−2Na+2H−H]$^-$ 481, found 481.

Materials and Methods

The compounds provided herein can be prepared from readily available starting materials using the following general methods and procedures, for example, as described in WO 2013/036835 and WO 2014/160480. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB—H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 0.5 to about 4 ppm) will be understood to be an exemplary interpretation of the NMR spectrum (e.g., exemplary peak integratations) of a compound. Exemplary general method for preparative HPLC: Column: Waters RBridge prep 10 µm C18, 19*250 mm. Mobile phase: acetonitrile, water ($NH_4HCO_3$) (30 L water, 24 g $NH_4HCO_3$, 30 mL $NH_3.H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 µm at 45 C.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing"

are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound selected from the group consisting of:

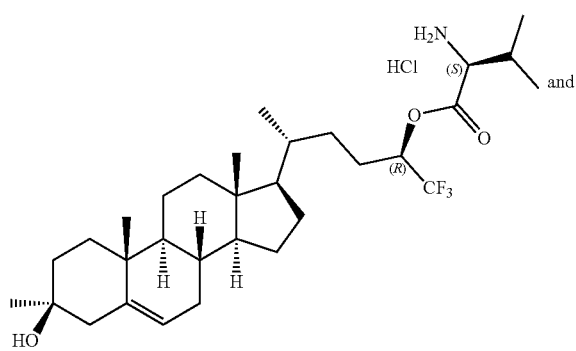

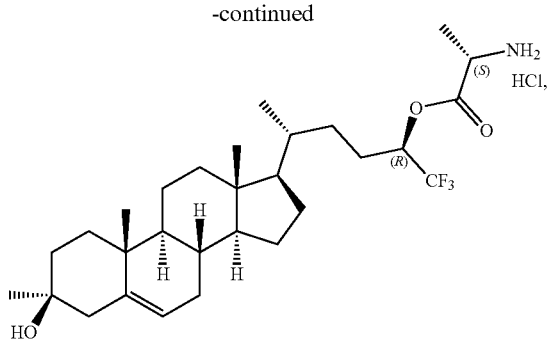

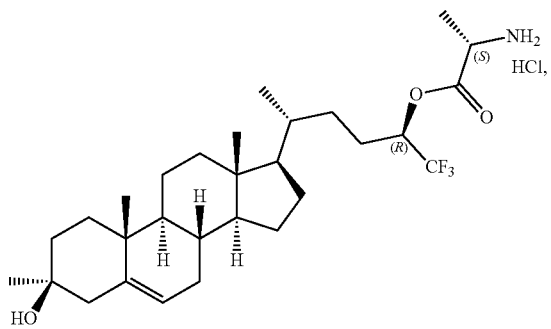

or a pharmaceutically acceptable salt thereof.

2. A pharmaceutical composition comprising a compound of claim 1 or a pharmaceutically acceptable salt thereof and a pharmaceutically acceptable carrier.

3. A method of inducing sedation or anesthesia comprising administering to a subject an effective amount of a compound of claim 1, or a pharmaceutically acceptable salt thereof, or pharmaceutical composition thereof.

* * * * *

UNITED STATES PATENT AND TRADEMARK OFFICE
CERTIFICATE OF CORRECTION

PATENT NO. : 10,696,712 B2  
APPLICATION NO. : 15/742422  
DATED : June 30, 2020  
INVENTOR(S) : Salituro et al.

Page 1 of 1

It is certified that error appears in the above-identified patent and that said Letters Patent is hereby corrected as shown below:

In the Claims

In Claim 1, at Column 84, Lines 20-35, delete:

" 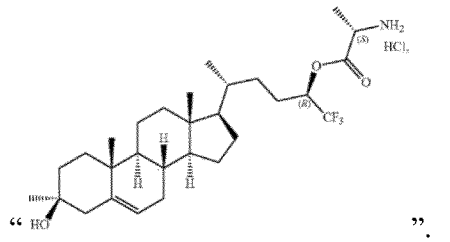 ".

Signed and Sealed this  
Ninth Day of August, 2022

Katherine Kelly Vidal  
*Director of the United States Patent and Trademark Office*